US009732281B2

(12) United States Patent
Kresnyak

(10) Patent No.: US 9,732,281 B2
(45) Date of Patent: *Aug. 15, 2017

(54) PROCESS FOR CO-PRODUCING COMMERCIALLY VALUABLE PRODUCTS FROM BYPRODUCTS OF HEAVY OIL AND BITUMEN UPGRADING PROCESS

(71) Applicant: Expander Energy Inc., Calgary (CA)

(72) Inventor: Steve Kresnyak, Calgary (CA)

(73) Assignee: Expander Energy Inc., Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/844,055

(22) Filed: Sep. 3, 2015

(65) Prior Publication Data
US 2016/0362610 A1 Dec. 15, 2016

Related U.S. Application Data

(63) Continuation of application No. 14/520,040, filed on Oct. 21, 2014, now Pat. No. 9,156,691, which is a continuation-in-part of application No. 13/091,025, filed on Apr. 20, 2011, now Pat. No. 9,169,443.

(51) Int. Cl.
| *C10G 2/00* | (2006.01) |
| *C10G 45/00* | (2006.01) |
| *C01B 3/34* | (2006.01) |
| *C10G 45/58* | (2006.01) |
| *C10G 21/00* | (2006.01) |
| *C10G 67/04* | (2006.01) |
| *C01B 21/087* | (2006.01) |
| *C07C 1/04* | (2006.01) |
| *C07C 29/151* | (2006.01) |
| *C07C 273/04* | (2006.01) |
| *C01B 3/38* | (2006.01) |
| *C10J 3/00* | (2006.01) |
| *C10K 3/06* | (2006.01) |
| *C10G 47/00* | (2006.01) |
| *C01B 3/50* | (2006.01) |
| *C01B 3/52* | (2006.01) |
| *C01B 3/56* | (2006.01) |
| *C01B 31/20* | (2006.01) |
| *C10G 7/00* | (2006.01) |
| *C10G 9/00* | (2006.01) |

(52) U.S. Cl.
CPC ............... *C10G 2/30* (2013.01); *C01B 3/34* (2013.01); *C01B 3/382* (2013.01); *C01B 3/384* (2013.01); *C01B 3/501* (2013.01); *C01B 3/52* (2013.01); *C01B 3/56* (2013.01); *C01B 21/087* (2013.01); *C01B 31/20* (2013.01); *C07C 1/0485* (2013.01); *C07C 29/1518* (2013.01); *C07C 273/04* (2013.01); *C10G 7/00* (2013.01); *C10G 9/00* (2013.01); *C10G 21/003* (2013.01); *C10G 45/00* (2013.01); *C10G 45/58* (2013.01); *C10G 47/00* (2013.01); *C10G 67/049* (2013.01); *C10J 3/00* (2013.01); *C10K 3/06* (2013.01); *C01B 2203/0205* (2013.01); *C01B 2203/0233* (2013.01); *C01B 2203/0244* (2013.01); *C01B 2203/0255* (2013.01); *C01B 2203/0283* (2013.01); *C01B 2203/043* (2013.01); *C01B 2203/0405* (2013.01); *C01B 2203/0475* (2013.01); *C01B 2203/062* (2013.01); *C01B 2203/1047* (2013.01); *C01B 2203/1082* (2013.01); *C01B 2203/1211* (2013.01); *C01B 2203/141* (2013.01); *C10G 2300/1022* (2013.01); *C10G 2300/1077* (2013.01); *C10G 2300/206* (2013.01); *C10G 2300/42* (2013.01); *C10J 2300/0913* (2013.01); *C10J 2300/0959* (2013.01); *C10J 2300/1659* (2013.01); *Y02P 30/10* (2015.11); *Y02P 30/30* (2015.11); *Y02P 30/44* (2015.11)

(58) Field of Classification Search
CPC .............. C10G 2/30; C10G 2300/1022; C10G 2300/1077; C01B 3/382; C01B 2203/0233; C01B 2203/0244; C01B 2203/0283; C01B 2203/0405; C01B 2203/043; C01B 3/025; C10K 3/06; C07C 273/04; C07C 29/153; C10J 3/00
USPC ...... 518/700, 702, 705; 423/359; 564/67, 69
See application file for complete search history.

(56) References Cited

U.S. PATENT DOCUMENTS

| 2,574,469 A | 11/1951 | Dressler et al. |
| 3,351,563 A | 11/1967 | Negra et al. |
| 3,941,820 A | 3/1976 | Jackson et al. |
| 4,217,112 A | 8/1980 | Johanson |
| 4,234,412 A | 11/1980 | Boersma et al. |

(Continued)

FOREIGN PATENT DOCUMENTS

| CA | 2320509 | 8/1999 |
| CA | 2595880 | 12/2005 |

(Continued)

OTHER PUBLICATIONS

Daniel B. Gillis and Fred Van Tine, What's New in Solvent Deasphalting? Foster Wheeler International Corporation, Heavy Oils Conference, Jun. 1998, pp. 16-1 to 16-13.

(Continued)

*Primary Examiner* — Jafar Parsa
(74) *Attorney, Agent, or Firm* — MBM Intellectual Property Law LLP

(57) ABSTRACT

The present invention is directed to modifications of bitumen and heavy oil upgrading and refining processes to synthesize synthetic crude oil and other valuable synthesized hydrocarbon products in an efficient manner along with the production of commercially valuable co-products from by-products formed by the upgrading process.

20 Claims, 10 Drawing Sheets

(56) References Cited

U.S. PATENT DOCUMENTS

| | | |
|---|---|---|
| 4,592,827 A | 6/1986 | Galiasso et al. |
| 5,378,348 A | 1/1995 | Davis et al. |
| 5,494,653 A | 2/1996 | Paisley |
| 6,043,288 A | 3/2000 | DeGeorge et al. |
| 6,048,449 A | 4/2000 | Bogdan et al. |
| 6,183,627 B1 | 2/2001 | Friday et al. |
| 6,241,874 B1 | 6/2001 | Wallace et al. |
| 6,306,917 B1 | 10/2001 | Bohn et al. |
| 6,395,944 B1 | 5/2002 | Griffiths et al. |
| 6,512,018 B2 | 1/2003 | Kennedy |
| 6,531,516 B2 | 3/2003 | Davis et al. |
| 6,540,023 B2 | 4/2003 | Davis et al. |
| RE38,170 E | 7/2003 | DeGeorge et al. |
| 6,596,780 B2 | 7/2003 | Jahnke et al. |
| 6,602,404 B2 | 8/2003 | Walsh et al. |
| 6,656,343 B2 | 12/2003 | Dancuart |
| 6,693,138 B2 | 2/2004 | O'Rear |
| 6,696,501 B2 | 2/2004 | Schanke et al. |
| 6,702,936 B2 | 3/2004 | Rettger et al. |
| 6,730,285 B2 | 5/2004 | Aasberg-Petersen et al. |
| 6,765,025 B2 | 7/2004 | Ding et al. |
| 6,863,802 B2 | 3/2005 | O'Rear et al. |
| 6,872,753 B2 | 3/2005 | Landis et al. |
| 6,929,087 B1 | 8/2005 | Sheppard |
| 6,958,363 B2 | 10/2005 | Espinoza et al. |
| 7,004,985 B2 | 2/2006 | Wallace et al. |
| 7,208,530 B2 | 4/2007 | Norbeck et al. |
| 7,214,720 B2 | 5/2007 | Bayle et al. |
| 7,381,320 B2 | 6/2008 | Iqbal et al. |
| 7,407,571 B2 | 8/2008 | Rettger et al. |
| 7,413,647 B2 | 8/2008 | Calderon et al. |
| 7,566,394 B2 | 7/2009 | Koseoglu |
| 7,677,309 B2 | 3/2010 | Shaw et al. |
| 7,708,877 B2 | 5/2010 | Farshid et al. |
| 7,749,378 B2 | 7/2010 | Iqbal et al. |
| 7,776,114 B2 | 8/2010 | Rüger et al. |
| 7,795,317 B2 | 9/2010 | Ellers et al. |
| 7,795,318 B2 | 9/2010 | Van Hardeveld |
| 7,846,979 B2 | 12/2010 | Rojey et al. |
| 7,855,235 B2 | 12/2010 | Van Hardeveld |
| 7,863,341 B2 | 1/2011 | Routier |
| 7,879,919 B2 | 2/2011 | Ernst et al. |
| 2001/0051662 A1 | 12/2001 | Arcuri et al. |
| 2003/0221992 A1 | 12/2003 | Gorbaty et al. |
| 2004/0181313 A1 | 9/2004 | Mohedas et al. |
| 2005/0250862 A1 | 11/2005 | Bayle et al. |
| 2006/0167118 A1 | 7/2006 | Tijm et al. |
| 2006/0231455 A1 | 10/2006 | Olsvik et al. |
| 2008/0021119 A1 | 1/2008 | Norbeck et al. |
| 2008/0021122 A1 | 1/2008 | Norbeck et al. |
| 2008/0115415 A1 | 5/2008 | Agrawal et al. |
| 2008/0116111 A1 | 5/2008 | Newton et al. |
| 2009/0012188 A1 | 1/2009 | Rojey et al. |
| 2009/0084707 A1 | 4/2009 | Gil et al. |
| 2009/0200209 A1 | 8/2009 | Sury et al. |
| 2009/0292571 A1 | 11/2009 | Gil et al. |
| 2010/0000153 A1 | 1/2010 | Kurkjian et al. |
| 2010/0036181 A1 | 2/2010 | Diebold et al. |
| 2010/0113624 A1 | 5/2010 | Routier et al. |
| 2010/0137458 A1 | 6/2010 | Erling et al. |
| 2010/0144905 A1 | 6/2010 | Reaveley et al. |
| 2010/0216898 A1 | 8/2010 | Tonseth et al. |
| 2011/0009501 A1 | 1/2011 | Ernst et al. |
| 2011/0049016 A1 | 3/2011 | McGrady et al. |

FOREIGN PATENT DOCUMENTS

| | | |
|---|---|---|
| CA | 2657656 | 1/2008 |
| CA | 2731376 | 6/2010 |
| CA | 2737872 | 4/2011 |
| CA | 2809503 | 3/2013 |
| CA | 2818322 | 4/2014 |
| CN | 101864324 | 10/2010 |
| CN | 101864324 A | 10/2010 |
| EP | 1608924 | 9/2007 |
| RU | 2364616 | 8/2009 |
| RU | 2364616 C1 | 8/2009 |
| WO | 2007009951 | 1/2007 |

OTHER PUBLICATIONS

Wassim Bedrouni, Bitumen Extraction and Upgrading Coke Gasification with CO2 Capture, 2008, Odec.

Tom Kemp, Prospects for the Future Oils Sands Production (presentation), Jacobs Engineering Canada, Syngas Refiner Oil Sands Workshop, Calgary, Alberta, Canada, Jul. 27, 2006.

Gary, J.H. et al., Petroleum Refining Technology and Economics, 5th ed, CRC Press, 2007, 465 pgs [Office Action cites figure 1.1].

T.F. Yen, Correlation Between Heavy Crude Sources and Types and Their Refining and Upgrading Methods, No. 1998231, Proceeding of the 7th Unitar International Conference on Heavy Crude and Tar Sands, Beijing, vol. 2, pp. 2137-2144 (1998).

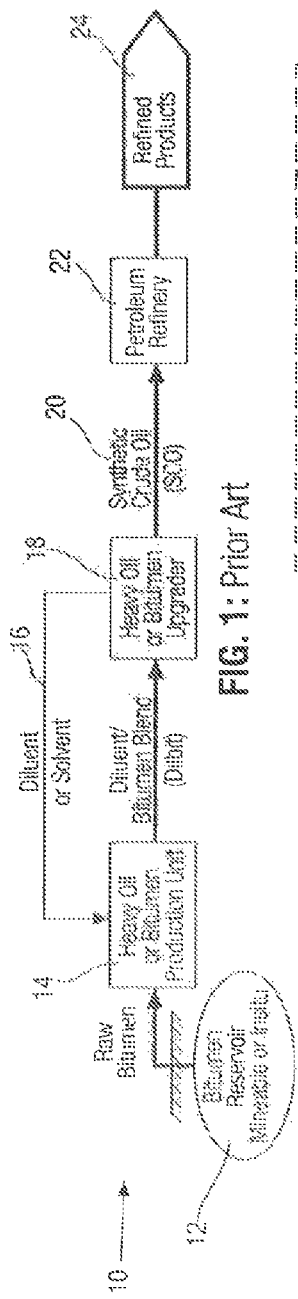
FIG. 1: Prior Art
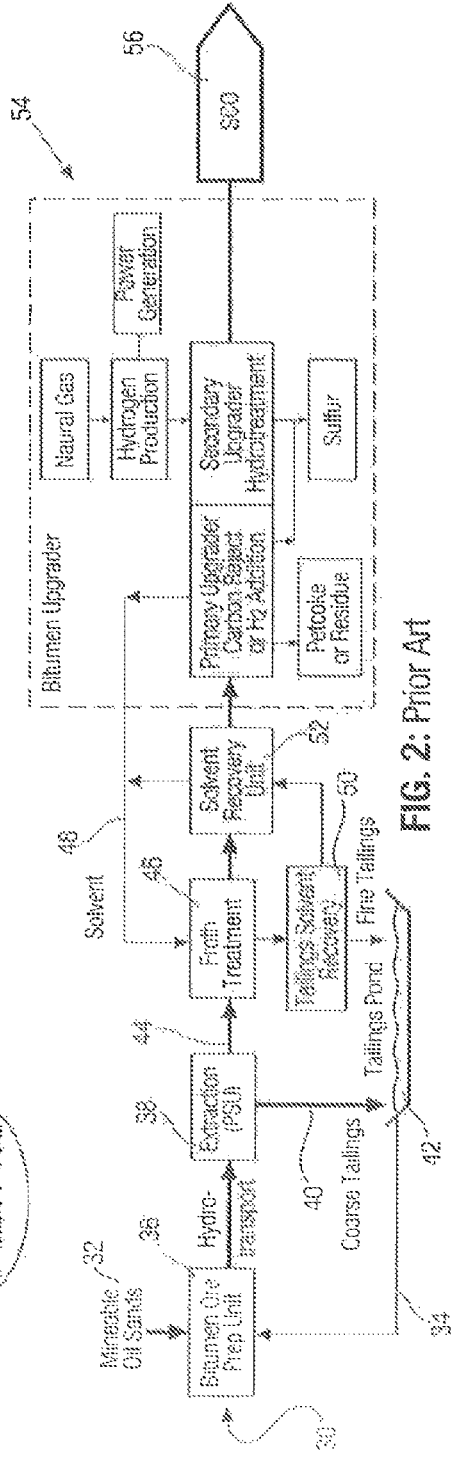
FIG. 2: Prior Art
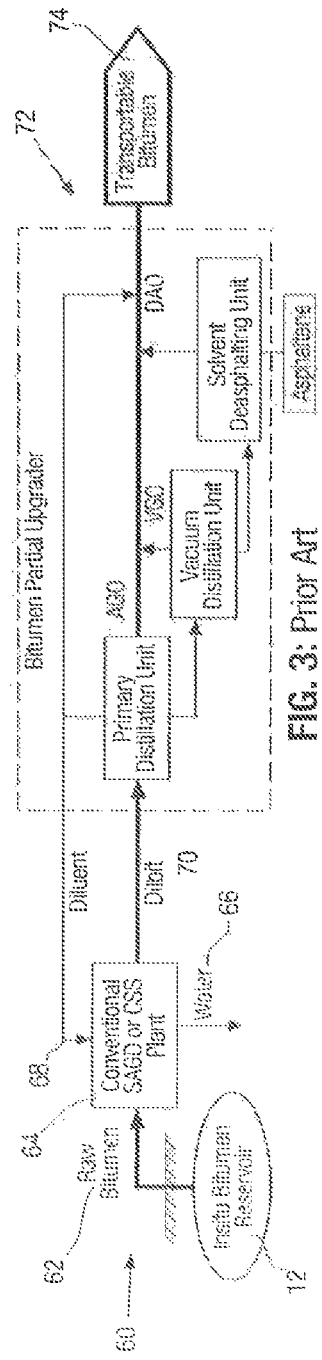
FIG. 3: Prior Art

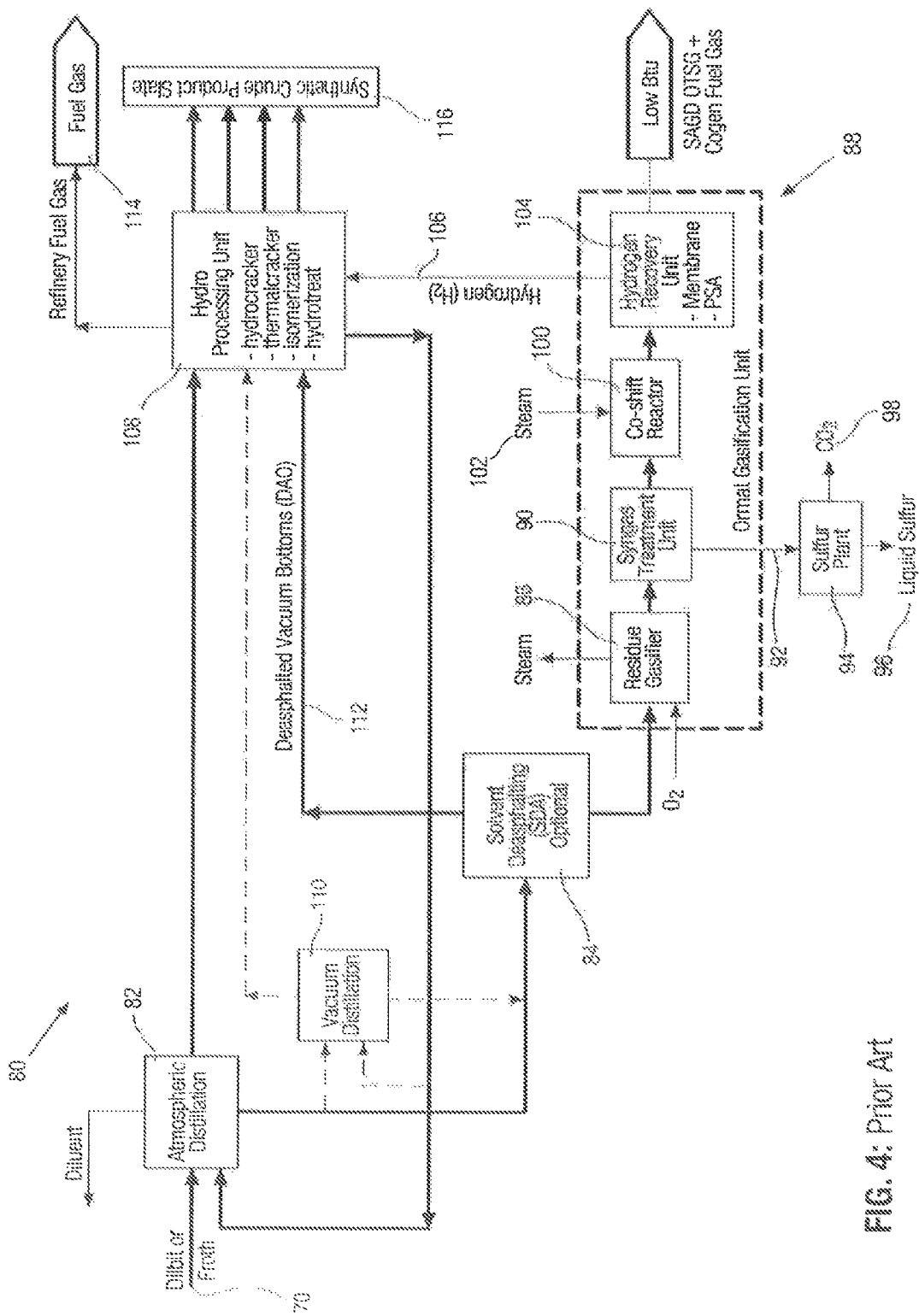
FIG. 4: Prior Art

METHANOL CO-PRODUCTION PROCESS

AMONIA CO-PRODUCTION PROCESS

COMBINED CO-PRODUCTION PROCESS

PROCESS FOR CO-PRODUCING COMMERCIALLY VALUABLE PRODUCTS FROM BYPRODUCTS OF HEAVY OIL AND BITUMEN UPGRADING PROCESS

CROSS-REFERENCE TO RELATED APPLICATIONS

This application is a continuation of U.S. application ser. No. 14/520,040 filed Oct. 21, 2014, which issued as U.S. Pat. No. 9,156,691 Oct. 13, 2015, and a continuation-in-part of U.S. application Ser. No. 13/091,025 filed Apr. 20, 2011, which issued as U.S. Pat. No. 9,169,443 Oct. 27, 2015. The contents of the aforementioned applications are hereby expressly incorporated by reference in their entirety for all purposes.

TECHNICAL FIELD

The present invention relates to modifications of bitumen and heavy oil upgrading and refining processes to synthesize synthetic crude oil and other valuable synthesized hydrocarbon products in an efficient manner along with the production of commercially valuable co-products from byproducts formed by the upgrading process.

BACKGROUND OF THE INVENTION

It is well established that certain forms of hydrocarbons require upgrading in order to either transport them or enhance value for sale. Further, refineries are not suited to processing heavy oil, bitumen etc. and thus the viscosity, density and impurity content, such as heavy metals, sulfur and nitrogen, present in such heavy materials must be altered to permit refining. Upgrading is primarily focused upon reducing viscosity, sulphur, metals, and asphaltene content in the bitumen.

One of the problems with heavy oil and bitumen upgrading is that the asphaltenes and the heavy fraction must be removed or modified to create value and product yield. Typical upgraders exacerbate the problem by the formation of petcoke or residuum which results in undesirable waste material. This material, since it cannot be easily converted by conventional methods, is commonly removed from the process, reducing the overall yield of valuable hydrocarbon material from the upgrading process.

The Fischer-Tropsch process has found significant utility in hydrocarbon synthesis procedures and fuel synthesis. The process has been used for decades to assist in the formulation of hydrocarbons from several materials such as coal, residuum, petcoke, and biomass. In the last several years, the conversion of alternate energy resources has become of great interest, given the escalating environmental concerns regarding pollution, the decline of world conventional hydrocarbon resources, and the increasing concern over tailings pond management, together with the increasing costs to extract, upgrade and refine the heavy hydrocarbon resources. The major producers in the area of synthetic fuels have expanded the art significantly in this technological area with a number of patented advances and pending applications in the form of publications. Applicant's co-pending U.S. application Ser. No. 13/024,925, teaches a fuel synthesis protocol and the entire contents of that application are incorporated herein for reference.

Examples of recent advances that have been made in this area of technology includes the features taught in U.S. Pat. No. 6,958,363, issued to Espinoza, et al., Oct. 25, 2005, Bayle et al., in U.S. Pat. No. 7,214,720, issued May 8, 2007, U.S. Pat. No. 6,696,501, issued Feb. 24, 2004, to Schanke et al.

In respect of other progress that has been made in this field of technology, the art is replete with significant advances in, not only gasification of solid carbon feeds, but also methodology for the preparation of syngas, management of hydrogen and carbon monoxide in a GTL plant, the Fischer-Tropsch reactors management of hydrogen, and the conversion of biomass feedstock into hydrocarbon liquid transportation fuels, inter alia. The following is a representative list of other such references. This includes: U.S. Pat. Nos. 7,776,114; 6,765,025; 6,512,018; 6,147,126; 6,133,328; 7,855,235; 7,846,979; 6,147,126; 7,004,985; 6,048,449; 7,208,530; 6,730,285; 6,872,753, as well as United States Patent Application Publication Nos. US2010/0113624; US2004/0181313; US2010/0036181; US2010/0216898; US2008/0021122; US 2008/0115415; and US 2010/0000153.

The Fischer-Tropsch (FT) process has several significant benefits when applied to a bitumen upgrading and refinery processes, one benefit being that it is able to convert previously generated petcoke and residuum to valuable, high quality synthetic crude oil (SCO) with notably increased paraffinic content. A further significant benefit is that the raw bitumen yield to SCO is near or greater than 100%, a 20% yield increase relative to certain current upgrader processes. Another benefit is that there is no petcoke and residuum waste product to impact the environment thus improving overall bitumen resource utilization. Similar effects can also be achieved with the current refinery processes.

A further benefit of the application of the FT process to a bitumen upgrader is that a sweet, highly paraffinic and high cetane content synthetic crude oil (SCO) is produced. More specifically, beneficial products of the FT process such as paraffinic naphtha and FT vapours (such as methane and liquid petroleum gases (LPG)), have particular value within the bitumen upgrader process and upstream unit operations. FT vapours, virtually free from sulphur compounds can be used as upgrader fuel or as feedstock for hydrogen generation to offset the requirement for natural gas. FT naphtha, primarily paraffinic in nature, can also be used in the generation of hydrogen, but further, due to its unique paraffinic nature, it can also be used as an efficient deasphalting solvent not readily available from current upgrader operations.

It has also been well documented that the use of FT paraffinic naphtha as a solvent for an oilsands froth unit improves the operation and efficacy of fine tailings and water removal at a reduced diluent-to-bitumen (D/B) ratio and relatively low vapour pressure. This has significant advantages in terms of lowering the size and cost of expensive separators and settlers and increasing their separation performance and capacity rating. This results in virtually dry bitumen froth feed (<0.5 basic sediment and water) to the upgrader, while improving impact on the tailings pond.

Having thus generally discussed the appropriateness of the Fischer-Tropsch technique in synthesizing syngas to FT liquids, a discussion of the prior art and particularly the art related to the upgrading and gasifying of heavy hydrocarbon feeds would be useful.

One of the examples in this area of the prior art is the teachings of U.S. Pat. No. 7,407,571 issued Aug. 5, 2008, to Rettger et. al. This reference names Ormat Industries Ltd. as the Assignee and teaches a process for producing sweet synthetic crude oil from a heavy hydrocarbon feed. In the method, the patentees indicate that heavy hydrocarbon is upgraded to produce a distillate feed which includes sour products and high carbon products. The high carbon content products are gasified in a gasifier to produce a syngas and sour products. The process further hydroprocesses the sour products along with hydrogen gas to produce gas and a sweet crude. Hydrogen is recovered in a recovery unit from the synthetic fuel gas. The process also indicates that further hydrogen gas is processed and hydrogen depleted synthetic fuel gas is also produced. Further hydrogen gas is supplied to the hydroprocessing unit and a gasifying step is conducted in the presence of air or oxygen. The gas mixture is scrubbed to produce a sour water and a clean sour gas mixture. The sour gas mixture is subsequently processed to produce a sweet synthetic fuel gas and a hydrogen enriched gas mixture from the synthetic fuel gas using a membrane. The overall process is quite effective, however, it does not take advantage of the conversion of synthesized streams which are useful for introduction into the hydroprocessing unit for production of synthetic crude, the recycling of unique streams for use in the upgrader, nor is there any teaching specifically of the integration of the Fischer-Tropsch process or the recognition of the benefit to the process of using a SMR and/or ATR in the process circuit to maximize SCO yields and reducing dependence on natural gas.

Iqbal et al. in U.S. Pat. No. 7,381,320 issued Jun. 3, 2008, teaches a process for heavy oil and bitumen upgrading. In overview, the process is capable of upgrading crude oil from a subterranean reservoir. The process involves converting asphaltenes to steam power, fuel gas, or a combination of these for use in producing heavy oil or bitumen from a reservoir. A portion of the heavy oil or bitumen are solvent deasphalted to form an asphaltene fraction and a deasphalted oil, referred to in the art as DAO as a fraction free of asphaltenes and with reduced metals content. The asphaltene fraction from the solvent deasphalting is supplied to the asphaltenes conversion unit and a feed comprising the DAO fraction supplied to a reaction zone of a fluid catalytic cracking (FCC) unit with an FCC catalyst to capture a portion of the metals from the DAO fraction. A hydrocarbon effluent is recovered from this having a reduced metal content. Similar to the process taught in U.S. Pat. No. 7,407,571, this process has utility, however, it limits the conversion of the otherwise wasteful asphaltene to production of solid fuel or pellets or conversion to syngas for fuel, hydrogen or electric power production. There is no teaching specifically integrating the Fischer-Tropsch process.

In U.S. Pat. No. 7,708,877 issued May 4, 2010 to Farshid et al. there is taught an integrated heavy oil upgrader process and in line hydro finishing process. In the process, a hydroconversion slurry reactor system is taught that permits a catalyst, unconverted oil and converted oil to circulate in a continuous mixture throughout a reactor with no confinement of the mixture. The mixture is partially separated between the reactors to remove only the converted oil while allowing unconverted oil in the slurry catalyst to continue on to the next sequential reactor where a portion of the unconverted oil is converted to a lower boiling point. Additional hydro processing occurs in additional reactors for full conversion of the oil. The so called fully converted oil is subsequently hydrofinished for nearly complete removal of heteroatoms such as sulfur and nitrogen.

This document is primarily concerned with hydroconversion of heavy hydrocarbon, while not being suitable for bitumen upgrading. It also fails to provide any teaching regarding the use of Fischer-Tropsch process, usefulness of recycle streams, hydrogen generation or other valuable and efficient unit operations critical to successful upgrading of raw bitumen.

Calderon et al. in U.S. Pat. No. 7,413,647 issued Aug. 19, 2008, teach a method and apparatus for upgrading bituminous material. The method involves a series of four distinct components, namely a fractionator, a heavy gas oil catalytic treater, a catalyst regenerator/gasifier and a gas clean up assembly. The patent indicates that in practicing the method, the bitumen in liquid form is fed to the fractionator for primary separation of fractions with the bulk of the bitumen leaving the bottom of the fractionator in the form of a heavy gas oil which is subsequently pumped to the catalytic treater and sprayed on a hot catalyst to crack the heavy gas oil, thus releasing hydrocarbons in the form of hydrogen rich volatile matter while depositing carbon on the catalyst. The volatile matter from the treater is passed to the fractionator where condensable fractions are separated from noncondensable hydrogen rich gas. The carbon containing catalyst from the treater is recycled to the regenerator/gasifier and the catalyst, after being regenerated is fed hot to the treater.

The method does not incorporate the particularly valuable Fischer-Tropsch process or provide a unit for effecting the Fischer-Tropsch reaction and further, the method is limited by the use of the catalyst which would appear to be quite susceptible to sulfur damage and from this sense there is no real provision for handling the sulfur in the bitumen.

In United States Patent Application, Publication No. US 2009/0200209, published Aug. 13, 2009, Sury et al. teach upgrading bitumen in a paraffinic froth treatment process. The method involves adding a solvent to a bitumen froth emulsion to induce a settling rate of at least a portion of the asphaltenes and mineral solids present in the emulsion and results in the generation of the solvent bitumen-froth mixture. Water droplets are added to the solvent bitumen-froth mixture to increase the rate of settling of the asphaltenes and mineral solids. The focus of the publication is primarily to deal with the froth. There is no significant advance in the upgrading of the bitumen.

A wealth of advantages are derivable from the technology that has been developed and which is described in copending U.S. Ser. No. 13/091,025. These are realized in a number of ways including:

i) near 100% or greater synthetic crude yield from heavy oil or bitumen without the wasteful production of petcoke or residuum;

ii) the synthetic crude oil (SCO) slate is higher quality, sweet light crude with more paraffinic and less aromatic and heavy gas oil components in the product slate;

iii) less natural gas is required to generate hydrogen for upgrading as the FT naphtha, FT vapours and hydroprocessing vapours can be recycled to generate a hydrogen rich syngas;

iv) pure hydrogen can be generated from the hydrogen rich syngas using membranes, absorption or pressure swing adsorption units, for use in the hydroprocessing (hydrocracking, isomerisation, hydrotreating) units;

v) Fischer-Tropsch (FT) liquids are primarily pariffinic in nature improving the quality and value of SCO product slate;

vi) FT naphtha is rarely available in any quantity in current upgraders and would be very preferentially used for deasphalting vacuum bottoms in a Solvent Deasphalting Unit (SDA) and in a Oilsands Froth Treatment Unit; and vii) Concentrated $CO_2$ is available from the gasifier (XTL) syngas treatment unit, allowing the upgrader to be a low cost $CO_2$ source.

Although the processes disclosed in U.S. Ser. No. 13/091,025 allow for the conversion of about 90% of all carbon in the feed streams to hydrocarbon products, there remains a need for technology that provides for the conversion of the $CO_2$ and other by-products of the upgrading process to commercially valuable co-products. As part of the further advancements set forth herein, there are provided processes for the production of commercially useful co-products from the by-products of the upgrading process. These processes can be integrated within upgrading systems as described, for example, in co-pending U.S. Ser. No. 13/091,025.

SUMMARY OF THE INVENTION

One object of the present invention is to provide an improved heavy oil and bitumen upgrading methodology for synthesizing hydrocarbons with a substantially increased yield without the production of waste byproducts such as petcoke or residuum.

A further object of one embodiment of the present invention is to provide a process for co-producing commercially valuable co-products from by-products of a process for upgrading or refining heavy oil or bitumen to formulate synthesized hydrocarbons, comprising:
  (a) forming a non-distilled bottom fraction from a source of heavy oil or bitumen feedstock
  (b) feeding said bottom fraction to a syngas generating circuit for formulating a hydrogen lean syngas stream via a non-catalytic partial oxidation reaction;
  (c) providing a first hydrogen rich syngas stream from a syngas generator;
  (d) subjecting a portion of said first hydrogen rich syngas stream to a hydrogen separator unit to provide a purified hydrogen by-product stream and a second hydrogen rich syngas stream;
  (e) subjecting at least a portion of said hydrogen lean syngas stream, said first hydrogen rich syngas stream, said second hydrogen rich syngas stream or a combination thereof, to a carbon dioxide removal operation to obtain a purified hydrogen rich syngas stream and a carbon dioxide by-product stream;
  (e) reacting said purified hydrogen rich syngas stream in a Fischer-Tropsch reactor to formulate synthesized hydrocarbons; and
  (f) converting said purified hydrogen stream and/or said carbon dioxide by-product stream into said commercially valuable co-products.

Synthetic crude is the output from a bitumen/heavy oil upgrader facility used in connection with bitumen and heavy oil from mineable oil sands and in situ production. It may also refer to shale oil, an output from an oil shale pyrolysis. The properties of the synthetic crude depend on the processes used in the upgrading. Typically, it is low in sulfur and has an API gravity of around 30, suitable for conventional refinery feedstock. It is also known as "upgraded crude".

The present disclosure amalgamates a series of known unit operations into a much improved synthesis route for a high yield, high quality production of synthetic hydrocarbons and co-production of commercially valuable co-products from by-products of this synthetic route. Integration of a Fischer-Tropsch process, and more specifically the integration of a Fischer-Tropsch process with a hydrogen rich syngas generator which uses FT naphtha, FT LPG and/or FT/upgrader vapours as primary fuel in combination with natural gas, in a steam methane reformer (SMR) and/or an autothermal reformer (ATR) results in a superior sweet synthetic crude oil which is synthesizable in the absence of petcoke and residuum.

It was discovered that, by employing a steam methane reformer (SMR) as a hydrogen rich syngas generator using FT naphtha and FT/upgrader vapours, in combination with natural gas, significant results can be achieved when blended with the hydrogen lean syngas created by the gasification of non-distilled bitumen or heavy oil bottoms. A significant production increase in middle distillate synthetic hydrocarbons range is realized. The general reaction is as follows;

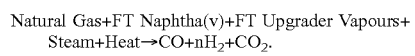
Natural Gas+FT Naphtha(v)+FT Upgrader Vapours+Steam+Heat→CO+$nH_2$+$CO_2$.

As is well known to those skilled in the art, steam methane reforming may be operated at any suitable conditions to promote the conversion of the feedstreams, an example as shown in above equation, to hydrogen $H_2$ and carbon monoxide CO, or what is referred to as syngas or specifically as hydrogen rich syngas. Significant benefits resulted in a great than 30% increase in middle distillate synthesized hydrocarbon. Steam and natural gas is added to optimize the desired ratio of hydrogen to carbon monoxide to approximate range of 3:1 to 7:1. A water gas shift reaction (WGS), pressure swing adsorption (PSA) or membrane unit can also be added to any portion of the SMR syngas circuit to further enrich the hydrogen rich stream and generate a near pure hydrogen stream for hydroprocessing use. Generally natural gas or any other suitable fuel is used to provide the heat energy for the SMR furnace.

The steam reformer may contain any suitable catalyst, an example of one or more catalytically active components such as palladium, platinum, rhodium, iridium, osmium, ruthenium, nickel, chromium, cobalt, cerium, lanthanum, or mixtures thereof. The catalytically active component may be supported on a ceramic pellet or a refractory metal oxide. Other forms will be readily apparent to those skilled.

It was further discovered that employing an autothermal reformer (ATR) as a sole hydrogen rich syngas generator or in any series or parallel combination with the SMR or as a hybrid combination of an ATR/SMR referred to as a XTR, significant benefits resulted in a greater than 200% increase in the FT middle distillate synthetic hydrocarbons. Feedstreams for the ATR or XTR consist of FT naphtha, FT LPG, FT vapours, $H_2$ rich upgrader vapours, Upgrader excess LPG, $CO_2$, $O_2$ and natural gas.

Similarly, as is well known to those skilled in the art, autothermal reforming ATR employs oxygen and carbon dioxide or steam, in a reaction with light hydrocarbon gases like natural gas, FT vapours, FT LPG and upgrader vapours and excess LPG to form syngas. This is an exothermic reaction in view of the oxidation procedure. When the autothermal reformer employs carbon dioxide, the hydrogen to carbon monoxide ratio produced is 1:1 and when the autothermal reformer uses steam, the ratio produced is approximately 2.5:1, or unusually as high as 3.5:1.

The reactions that are incorporated in the autothermal reformer are as follows:

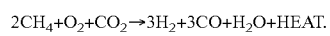
$2CH_4+O_2+CO_2 \rightarrow 3H_2+3CO+H_2O+HEAT$.

When steam is employed, the reaction equation is as follows:

$4CH_4+O_2+2H_2O+HEAT \rightarrow 10H_2+4CO$.

One of the more significant benefits of using the ATR is realized in the variability of the hydrogen to carbon monoxide ratio. In the instant technology, an ATR may also be considered as a hydrogen rich syngas generator, as described previously. It has been found that the addition of the ATR operation to the circuit in combination with the hydrogen rich syngas generation circuit, shown in the example above as a steam methane reformer (SMR), has a significant effect on the hydrocarbon productivity from the overall process. Similarly, a water gas shift reaction (WGS), pressure swing adsorption (PSA) or membrane unit can also be added to any portion of the ATR and combined ATR/SMR or XTR syngas circuit to further enrich the hydrogen rich stream and generate a near pure hydrogen stream for hydroprocessing use. Generally natural gas or any other suitable fuel is used to provide the heat energy for the ATR, SMR and XTR furnaces.

The present invention amalgamates previously unrecognized combinations in a heavy oil or bitumen upgrading process which expand the usefulness of the upgrading processes such as disclosed in the co-pending application Ser. No. 13/091,025, by providing a number of integrated strategies which are not available in stand-alone upgrading plants. In the process of the present application, in addition to the production of synthetic crude oil, synthetic diesel and synthetic jet streams, it is possible to convert excess or by-product $CO_2$, nitrogen ($N_2$) and hydrogen ($H_2$) to commercially valuable co-products.

Referring now to the drawings as they generally describe the invention, reference will now be made to the accompanying drawings illustrating preferred embodiments.

BRIEF DESCRIPTION OF THE DRAWINGS

FIG. 1 is a process flow diagram of methodology known in the prior art for processing of mineable and in situ heavy oil and bitumen;

FIG. 2 is a process flow diagram similar to FIG. 1, illustrating a further technique known in the art;

FIG. 3 is a process flow diagram illustrating a further variation of the prior art technology;

FIG. 4 is a process flow diagram illustrating a further variation of the prior art technology;

Similar numerals employed in the figures denote similar elements.

DETAILED DESCRIPTION OF PREFERRED EMBODIMENTS

Figure 5:
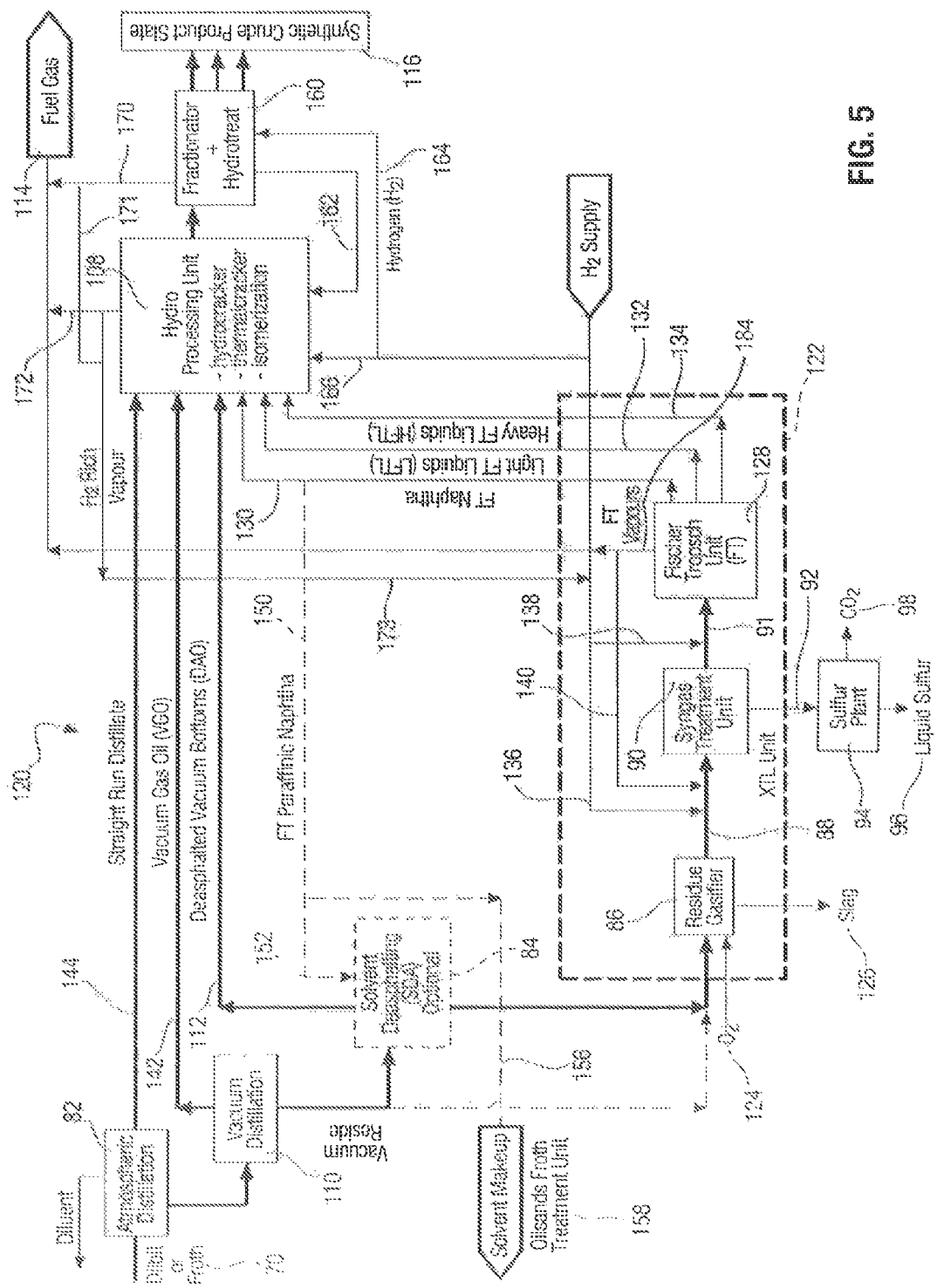
FIG. 5 is a process flow diagram illustrating an embodiment of the upgrading process.

Referring now to FIG. 1, shown is a first embodiment of a bitumen production flow diagram based on the prior art. The overall process is denoted by 10. In the process, the heavy oil or bitumen source 12 may comprise a bitumen reservoir which may be minable or in situ. Generally speaking, the bitumen then may be transported to a heavy oil or bitumen production unit 14 into which diluent or solvent may be introduced via line 16 from a heavy oil or bitumen upgrader 18. The diluent or solvent can comprise any suitable material well known to those skilled in the art such as suitable liquid alkanes as an example. Once the diluent is introduced via line 16 into the production unit 14, the result is a mobilizable bitumen blend (dilbit). Once the diluted bitumen blend is processed in the upgrader 18, the so formed synthetic crude, globally denoted by 20 is then treated in a petroleum refinery 22 where subsequently refined products are formulated and with the refined products being globally denoted by 24.

The production unit 14 primarily removes water and solids from the stream. The diluent or solvent 16 is added to the raw bitumen to provide for the necessary mobilization and separation parameters, primarily providing a reduction in viscosity. In a situation where the bitumen is an oilsand derived bitumen, water is added to the raw material to provide a slurry for transport to the extraction and froth treatment plant and upgrader 18, as further described in FIG. 2. Dewatered bitumen is then transported by pipeline (not shown) as a diluent blend or dilbit to the upgrader 18. The dry raw bitumen is treated to primary and secondary treatment to create a sweet or sour crude oil (SCO). The SCO is transported to the petroleum refinery 22 to be further processed into refined product 24 as indicated above, examples of which include transport fuel such as gasoline, diesel and aviation fuels, lube oils and other feedstocks for petrochemical conversion.

With respect to FIG. 2, shown is a schematic process flow diagram of oilsands operation for bitumen upgrading. The overall process in this flow diagram is indicated by 30. Other than the embodiment shown, the system relates to a minable oilsands bitumen production process where raw mined oilsands ore, generally denoted by 32, from the mine are mixed with water 34 in an ore preparation unit 36 and subsequently hydrotransported to a primary extraction plant, denoted by 38. In the extraction plant 38, the greater portion of water 34 and course tailings 40 are separated and returned to a tailings pond 42.

Partially dewatered bitumen, generally denoted by 44 is transferred to a froth treatment unit 46. This is where a solvent, typically highly aromatic naphtha (derived from bitumen) or paraffinic solvent (derived from natural gas liquids) is added at 48 to separate the remaining water and refined clays as well as fine tailings. The froth is then treated in a solvent recovery unit 40 where the majority of the solvent is recovered for recycle to the froth treatment unit. The separated fine tailings passes through a tailings solvent recovery unit 50 for final recovery of solvent. The fine tailings are transferred into the tailings pond 42. The clean dry froth is then introduced into the bitumen upgrader, generally denoted by 54 and illustrated in FIG. 2 in dashed line. Generally speaking the bitumen upgrader 54 incorporates two general processes, a primary and secondary upgrading. The primary upgrader typically consists of two processing methodologies. The first, namely, carbon rejection or coking where the heavy fraction of the bitumen is removed as petcoke. Generally, the synthetic crude oil yield is between about 80 to about 85% by volume and the remaining portion converted primarily by petcoke is returned for storage to the mine. Further the coking process is a severe processing method and leads to higher aromatic content in the synthetic crude oil. The second process, namely hydrogen addition, uses a slurry based catalytic hydroprocessing system with the addition of hydrogen to treat the bitumen blend and produce an asphaltene reject and synthetic crude oil product. The yield of the synthetic crude oil typically exceeds 100% due to product swelling.

The hydrocarbon product streams from primary upgrading are further treated in secondary upgrader, consisting of hydrotreating units using hydrogen to stabilize synthetic crude products generally indicated as 56 and reduce sulfur and nitrogen impurities. Natural gas is used in a hydrogen unit to generate hydrogen requirements for the upgrader and co-generate electric power for upgrader use. The overall operations in the bitumen upgrader are indicated within the dash lines and these operations are well known to those skilled in the art.

Turning to FIG. 3, shown is a further partial upgrading process known in the prior art, in this arrangement, the process flow diagram delineates an in situ bitumen production unit. The overall process is denoted by 60. In such an arrangement, the in situ heavy oil or bitumen is exposed to steam to extract the oil. The raw bitumen 62 is treated in a conventional SAGD or CSS plant 64 to remove water 66. Diluent 68 is typically added to raw bitumen 62 in plant 64 to create water oil separation and to further provide a diluted blend for pipeline transportation, more commonly referred to in the art as "dilbit" denoted by 70. The dilbit can be transported over long distances in a pipeline (not shown) to remote refineries where it is blended with conventional crude as a feedstock. More integrated configurations may use distillation, deasphalting or visbreaking, a processing to create a near bottomless sour heavy crude for feed to refineries. This operation creates an asphaltene or vacuum residue stream requiring disposal. This partially upgraded bitumen is suitable for pipeline transportation. Often some quantity of diluent is still required to meet crude pipeline specifications. The dilbit is processed in a bitumen partial upgrader denoted by 72 with the operations being shown within the dashed line box. The transportable bitumen is denoted by 74 in FIG. 3.

As will be appreciated by those skilled, the process variations shown in FIGS. 1 through 3 of existing bitumen and heavy oil production facilities either create a waste product such as petcoke or residuum which leads to significant losses or further requires significant quantities of hydrogen or diluent to upgrade the product in order to be suitable as a refinery feedstock. Essentially, the existing processes do not provide a technology capable of capturing the full intrinsic value of the bitumen or heavy oil and has resulted in environmental impact related to disposal and management of undesirable waste products.

Turning to FIG. 4, shown is a further variation in the prior art of an enhanced bitumen upgrading process. It is the subject matter of Canadian Patent No. 2,439,038 and its United States homolog, U.S. Pat. No. 7,407,571 issued to Rettger, et al. (Ormat Industries Ltd.).

The overall process is denoted by 80.

Dilbit or froth 70 is introduced into an atmospheric distillation unit 82 with the non-distilled heavy bottoms being transported and introduced into a solvent deasphalting unit (SDA) 84 and the asphaltene bottoms are then subsequently fed into a gasifier 86, which gasifier is within the Ormat gasification unit, globally denoted by 88. The deasphalted material, commonly denoted as DAO is transferred to the hydroprocessing unit 108 for upgrading to synthetic crude oil. As an option, there may be a vacuum distillation unit 110 in the circuit which may introduce captured vacuum gasoils for introduction into hydroprocessing unit 108. Similarly, the vacuum bottoms are introduced into the SDA 84 to optimize process configuration.

The sour syngas generated by the gasification unit is then passed into a syngas treater 90 for acid gas removal. The acid gas is removed at 92 and treated in sulfur plant 94 producing at least products such as liquid sulfur 96 and $CO_2$ 98. The treated or "sweet" syngas is then processed in a water gas shift reaction (WGS) process as denoted in the FIG. 4 and referred to as a CO shift reactor 100. Steam is augmented in the reactor 100. The water gas shift reaction is merely a shift from the CO to $CO_2$ to create a hydrogen rich syngas. The hydrogen rich syngas may be then further treated in a typical pressure swing unit (PSA) or a membrane unit where the hydrogen is concentrated to greater than 99 percent. It occurs in unit 104. The hydrogen generated by 104, denoted by 106 is then the feedstock for the hydroprocessing unit 108. Once the hydroprocessing occurs, the result is synthetic crude oil (SCO) denoted by 116 and fuel gas denoted by 114.

Returning briefly to the hydrogen recovery unit 104, the byproduct of the unit 104 is a tailgas or a low BTU syngas which is used in the SAGD thermal steam generators as fuel to offset the need for natural gas as the primary fuel. The process has merit in that if natural gas is in short supply or there can be significant historic price fluctuation, the enhanced upgrader process is less dependent on the natural gas and can rely on the synthesized fuel for the overall process benefits.

Turning to FIG. 5, shown as a first embodiment of an enhanced bitumen upgrading circuit process incorporating Fischer-Tropsch technology and hydrogen synthesis. The embodiment of the overall process is denoted by 120. The overall process is particularly beneficial relative to the processes that were previously proposed in the prior art in that sweet carbon rich syngas is not passed through a water gas shift reaction, as denoted as 100 in FIG. 4, but rather is supplemented with external hydrogen 138 to create the optimum syngas composition, typically a ratio of hydrogen to carbon monoxide of greater than 1.8:1 to 2.2:1, and preferred as 2:1 as feed to Fischer-Tropsch reactor for producing high quality paraffinic Fischer-Tropsch liquids.

It is by the recognition of the usefulness of the Fischer-Tropsch reactor together with the avoidance of waste petcoke/residuum generation and the subsequent hydrogen source addition to maximize conversion of gasified carbon, that draws the proposed interim technology into the realm of being economical, convenient and highly efficient given the yields that are generated for the synthetic crude oil (SCO).

As is evident, there are a number of unit operations which are common with those in the prior art, namely the atmospheric distillation, vacuum distillation, solvent deasphalting, hydroprocessing, gasification, and syngas treatment.

In the embodiment shown, the Ormat gasification, commonly denoted as unit 88 and discussed with respect to FIG. 4 is replaced with a further sequence of operations (the XTL operations) shown in dashed lines and indicated by 122. In this embodiment, the gasifier 86 converts the non-distilled bottoms residue with typically oxygen ($O_2$) 124 to generate a hydrogen lean or carbon rich syngas 88 having a hydrogen to carbon dioxide ratio in range of 0.5:1 to 1.5:1, more specifically about 1:1, an example of which is shown in Table 1.

TABLE 1

Typical XTL Gasifier Hydrogen Lean Syngas Compositions

| | Feedstock Type | | |
|---|---|---|---|
| Syngas Composition (mole %) | Heavy Fuel Oil | Vacuum Residue | Asphaltene |
| CarbonDioxide ($CO_2$) | 2.75% | 2.30% | 5.0% |
| Carbon Monoxide (CO) | 49.52% | 52.27% | 50.4% |
| Hydrogen ($H_2$) | 46.40% | 43.80% | 42.9% |
| Methane (CH4) | 0.30% | 0.30% | 0.3% |
| Nitrogen (+Argon)($N_2$) | 0.23% | 0.25% | 0.4% |
| Hydrogen Sulfide ($H_2S$) | 0.78% | 1.08% | 1.0% |

A common byproduct, containing heavy metals and ash, from the gasification is discharged as slag denoted as 126. The hydrogen lean syngas 88 is then passed into the syngas treatment unit 90 for removal of acid gases 92 to create a sweet hydrogen lean syngas 91. Additional scrubbing, adsorption and washing technologies (not shown), well known to those skilled in the art, are typically employed to ensure that the sweet syngas is void of contaminants such as sulfur compounds which will have significant detrimental impact on the Fischer-Tropsch catalyst. The acid gas is further treated in the sulfur plant 94 to generate elemental sulfur 96 and carbon dioxide ($CO_2$), as was the case with respect to the process of FIG. 4. The sweet hydrogen lean syngas 91 is then passed into a Fischer-Tropsch unit reactor denoted by 128. As a possibility, the hydrocarbon products that are formed subsequently to reaction within the Fischer-Tropsch reactor 128 includes Fischer-Tropsch vapours 184 (CO+$H_2$+C1+C2+C3+C4), naphtha 130, light Fischer-Tropsch liquids 132 (LFTL) and heavy Fischer-Tropsch liquids (HFTL) 134 or commonly known as FT wax.

In order to trim or improve the efficiency of the overall process, the XTL unit 122 and specifically in advance of the syngas treatment unit 90 and/or the Fischer-Tropsch reactor 128 may be augmented with an external supply of hydrogen, indicated by 136 and 138, respectively. Further, at least some of the vapour from the Fischer-Tropsch reactor may be reintroduced in advance of the syngas treatment unit 90 as indicated by 140, and/or be used a fuel 114 in the upgrader. The liquids 130, 132 and 134 are introduced into hydroprocessing unit 108. This may also be augmented by straight run distillate naphtha 144 may be introduced from atmospheric distillation operation 82, light vacuum gas oil (LVGO) 142 from the vacuum distillation operation 110 and optionally, deasphalted oil 112 (DAO) from the SDA unit 84. A range of hydroprocessing treatments 108, as an example, hydrocracking, thermal cracking, isomerization, hydrotreating and fractionation, may be applied to the combined streams, individually or in desired combinations, well known to those skilled in the art, to create at least the synthetic crude oil product 116. As further options, any portion of the Fischer-Tropsch naphtha 130 particularly the paraffinic naphtha indicated by 150 may be reintroduced into the deasphalting unit 84 at 152 or further distributed as the solvent make up 156 for introduction into the oilsands froth treatment unit (not shown but generally noted by 158).

Further, additional hydrogen may be introduced into the hydroprocessing unit 108 and hydrotreating unit 160 at 166 and 164. The hydrogen supply may be taken from the hydrogen supply noted herein previously. From each of the fractionator, hydrotreater 160, hydroprocessing unit 108 and Fischer-Tropsch unit 128, product from each of these operations denoted by 170 or 172, 174 respectively is introduced to fuel gas 114. Further, a portion of 172 and 170 rich in hydrogen may be combined with the hydrogen lean syngas at 88 or 91 to enrich this stream for optimum performance of the Fischer-Tropsch unit.

Figure 6:
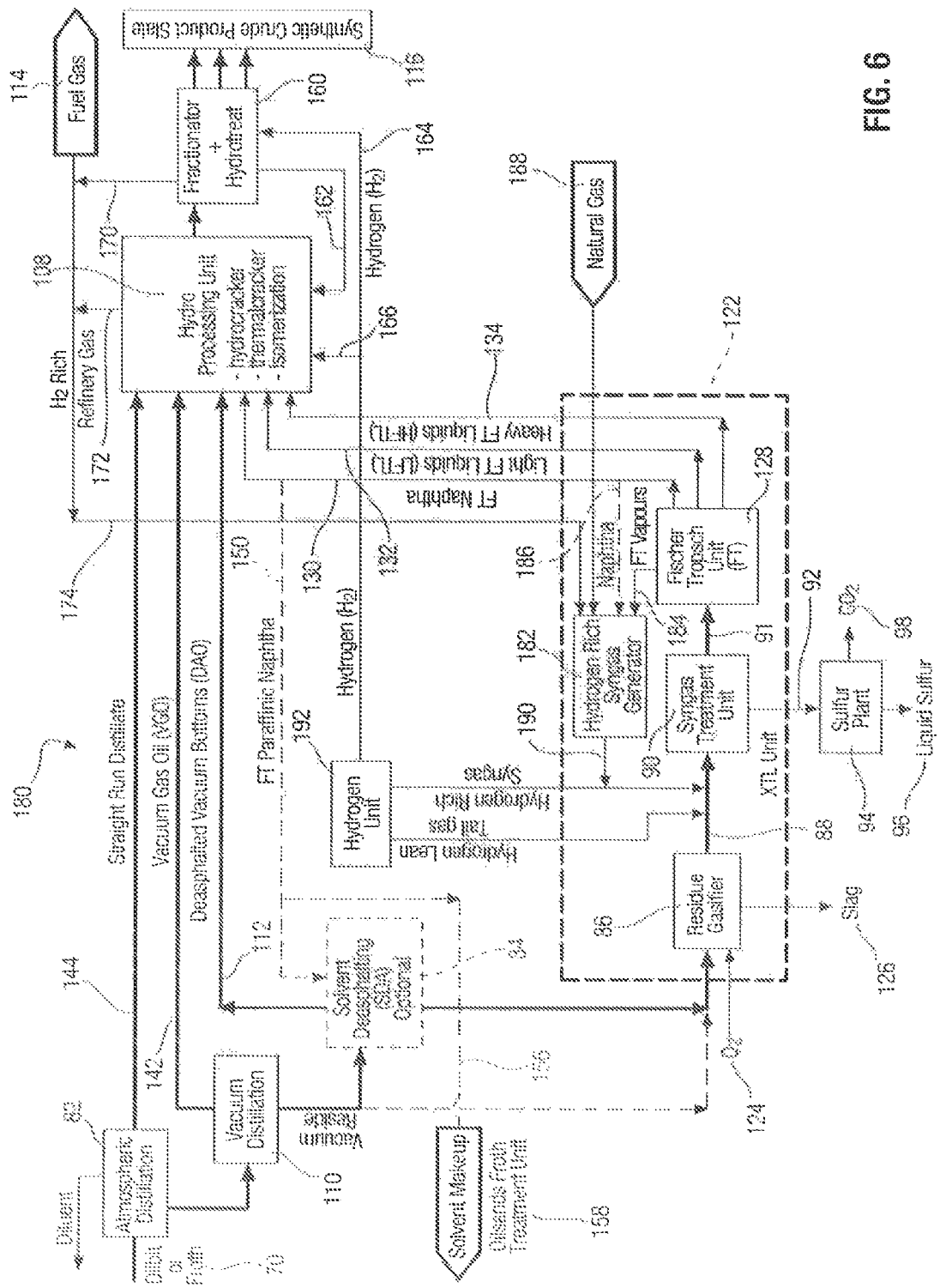
FIG. 6 is a process flow diagram illustrating a further embodiment of the upgrading process.

Turning to FIG. 6, shown in the process flow diagram is yet another variation on the methodology of the upgrading process. The overall process in this embodiment is denoted by 180. Similar unit operations from those established in FIGS. 4 and 5 are applicable in FIG. 6.

The primary changes with respect to FIG. 5 versus FIG. 6, includes modification of the XTL, unit 122 and incorporation of hydrogen rich syngas generation and recycle of hydrogen rich syngas generated in the Fischer-Tropsch unit 128.

In greater detail, the XTL, unit 122 is modified to incorporate a hydrogen rich syngas generator, denoted by 182. The hydrogen rich syngas generator 182 is typically composed of a steam methane reformer (SMR) (not shown) or an auto thermal reformer (ATR) (not shown) and combinations thereof. Natural gas 188, Fischer-Tropsch vapours 184, hydrogen rich fuel gas 174, etc. from the hydroprocessor 108 and fractionation unit 160 and Fischer-Tropsch naphtha 186 may be supplied individually or in combination to unit 122 to generate hydrogen rich syngas 190 where the ratio between the hydrogen and the carbon monoxide is in range of 2:5 to 6:1. Natural gas 188, depending on the current market situation at any location or time, may be used as a primary feedstock to the hydrogen rich syngas generator 182 and the streams 174, 130 and 184 may be used to maximize upgrader operation. Alternately, if the natural gas market is less favourable, streams 174, 130 and 184 may be fully utilized to offset the need for natural gas. The hydrogen rich syngas 190 can be introduced in advance of the syngas treatment unit 90 at 190 if treatment is required, or alternately, any portion of the hydrogen rich syngas 190 may be routed directly to the Ficher-Tropsch unit 128.

In this manner, the hydrogen rich syngas 190 is combined with the carbon rich syngas to create an optimum Fischer-Tropsch syngas where the ratio of the hydrogen to carbon monoxide is preferred 2:1. The combined feed streams to unit 122 reduces the amount of natural gas needed to achieve the optimum Fischer-Tropsch feed stream, thereby offering a commercial advantage of the upgraders dependence on natural gas, but also takes advantage of current low cost supply of natural gas.

Additionally, a portion of the hydrogen rich syngas 190 can be introduced to hydrogen unit 192 where a purified hydrogen stream 164 is generated for use in the hydroprocessing units 108 and 170. The hydrogen unit 192 may consist of a pressure swing adsorption (PSA), membrane or absorption technology, well known to those skilled in the art.

Figure 7:
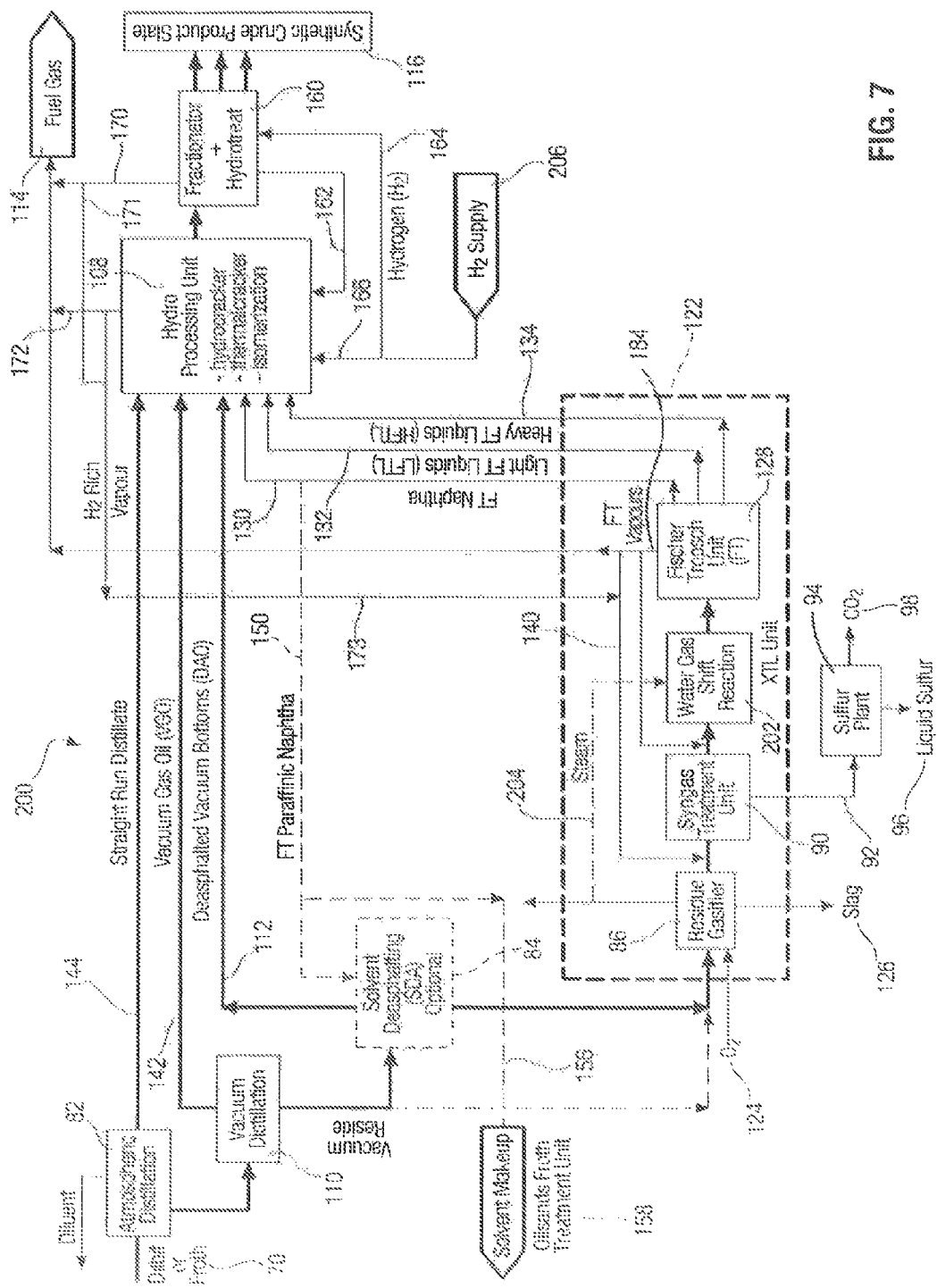
FIG. 7 is a process flow diagram illustrating yet another embodiment of the upgrading process.

Turning to FIG. 7, the process flow diagram illustrates a further variation on the overall concept of the upgrading process and in this manner, the XTL unit 122 undergoes further variation where the hydrogen unit 192 and hydrogen rich syngas generator 182 inherent in the embodiment FIG. 6 are replaced with a water gas shift (WGS) reaction unit operation. The overall process of FIG. 7 is denoted by 200. The water gas shift unit is denoted by 202 and is disposed between the syngas treatment unit 90 and the Fischer-Tropsch unit 128. As is known in the art and particularly by those skilled, the water gas shift reactor is useful to enrich the raw syngas which, in turn, results in optimization of the hydrogen to carbon monoxide ratio for the Fischer-Tropsch syngas. Steam supply for the WGS reaction unit 202 may be provided from the gasifier 86 shown as 204. Additionally, hydrogen rich gas 171 and 173 from the hydroprocessor units may be combined with the FT vapours 140 to enrich the FT syngas feed.

The upgrading process described herein and in co-pending application Ser. No. 13/091,025 is very efficient in retaining and managing carbon, and can produce a very high yield of conventional and synthetic hydrocarbon products while converting about 90% of the carbon in the feed streams. The unconverted carbon (about 10%) can be captured and commercially sold for commercial use or for enhanced oil recovery, or more typically sequestered or discharged to atmosphere as Green House Gases (GHG). The present invention provides a means for converting the by-product $CO_2$ into commercially valuable co-products. One embodiment of the present invention is to integrate a methanol ($CH_3OH$) synthesis unit to use all of the excess process and upgrader combustion derived $CO_2$ and any externally available $CO_2$, through reaction with portions of hydrogen rich syngas and purified hydrogen ($H_2$), in the production of these commercially valuable co-products.

The upgrading process described herein and in co-pending application Ser. No. 13/091,025 also uses high purity oxygen ($O_2$) in a Partial Oxidation Gasifier (POX Unit) to gasify the refinery or upgrader non-distillable bottoms or asphaltene stream which conventionally is converted to pet-coke or undesirable High Sulfur Fuel Oil (HSFO). Oxygen may also be used in the ATR syngas generator or for enrichment in the Claus sulfur plant (SRU). In one embodiment, an oxygen plant (ASU—Air Separation Unit) is used to separate air into near pure $O_2$ and near pure nitrogen ($N_2$) streams. This $N_2$ is typically partially or entirely vented to atmosphere if there is no commercial or refinery use. A further embodiment of the present invention is to integrate an ammonia ($NH_3$) synthesis unit to convert the excess $N_2$ into ammonia through reaction with purified hydrogen stream $H_2$. In another embodiment of the present invention, a portion of the ammonia is further converted to urea by reaction with by-product $CO_2$ in a urea synthesis unit.

The upgrading process, described herein and in co-pending application Ser. No. 13/091,025, uses a rich hydrogen syngas stream to optimize lean hydrogen syngas stream from POX Unit to feed an optimum $H_2$:CO ratio of 1.8 to 2.1, more preferred ratio of 2.0 to Fischer Tropsch (FT) Synthesis Unit. Simultaneously purified hydrogen ($H_2$) is produced from the Syngas Generators for Upgrader/Refinery Hydroprocessing use. Both the rich hydrogen syngas stream and purified hydrogen streams can be used as coincidental base feed streams for the methanol and ammonia co-production discussed above.

Common upgrading/refinery/complex process units, such as Syngas Generators, including Steam Methane Reformers (SMR), Auto-Thermal Reformers (ATR) and Partial Oxidizing gasifiers (POX), or combinations of above units can be used for the base upgrading/uprefinery complex and integrated for use as co-production syngas or hydrogen units for Ammonia and Methanol synthesis. The incremental increase in unit capacities provide economies of scale co-production that support lowest cost production.

In the process of the present invention near 100% of all the process carbon in feed streams, and by-product $CO_2$ streams captured from upgrading/refinery unconverted carbon streams, fuel gas streams and flue gas streams from combustion systems (i.e. furnaces, boilers, power generators) are converted to valuable commercial co-products.

Figure 8:
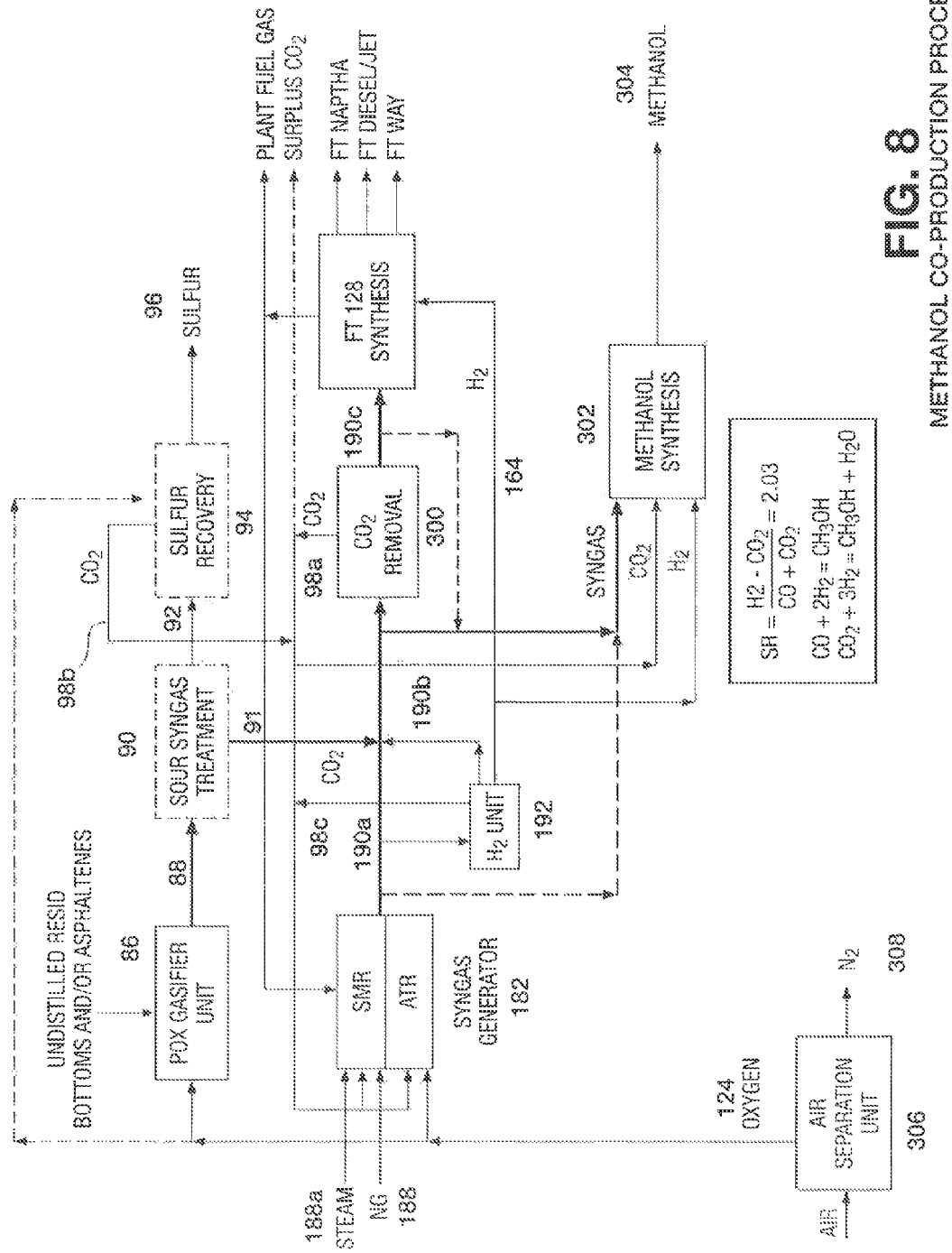
FIG. 8 is a process flow diagram illustrating integration of a methanol production unit with the upgrading process in accordance with the present invention.

FIG. 8 describes one configuration of the present invention whereby a Methanol Synthesis Unit receives base syngas feed from the Syngas Generators as described in FIG. 6, and is combined with the feed of excess $CO_2$ and $H_2$ to create the optimum methanol syngas feed stream, wherein optimum methanol synthesis stoichiometric ratio is defined as;

$$(H_2-CO_2)/(CO+CO_2)=2.03$$

With further processing the methanol can be used to produce numerous products such as DME gasoline/diesel, formaldehyde, MTBE, acetic acid, etc.

In further details, in the embodiment shown in FIG. 8, non-distillable heavy bottoms (from atmospheric distillation unit 82 or vacuum distillation unit 110), or the asphaltene stream from solvent deasphalting unit 84, is fed to gasifier 86 to generate a sour hydrogen lean syngas stream 88 via a non-catalytic partial oxidation reaction. The sour hydrogen lean syngas obtained from the gasifier 86 has a hydrogen to carbon monoxide ratio less than 1.0, typically 0.8 to 0.9. The sour hydrogen lean syngas stream is optionally passed through syngas treatment unit 90 to generate sweet lean syngas stream 91 and to remove acid gases 92 ($H_2S$ and $CO_2$). Additional scrubbing, adsorption and washing technologies (not shown), well known to those skilled in the art, are typically employed to ensure that the sweet syngas is void of contaminants such as sulfur compounds which will have significant detrimental impact on the Fischer-Tropsch catalyst.

As discussed with reference to FIG. 6, the upgrading process also includes a hydrogen rich syngas generator 182. The hydrogen rich syngas generator 182 is typically composed of a steam methane reformer (SMR) or an auto thermal reformer (ATR) or parallel or series combinations thereof. Alternatively, the syngas generator 182 can be as a hybrid combination of an ATR/SMR referred to as a XTR. The hydrogen rich syngas generator 182 produces a first hydrogen rich syngas stream 190a, where the ratio of hydrogen to carbon monoxide is in the range of 3:1 to 7:1. Natural gas 188 and steam 188a can be used as a feedstock to the hydrogen rich syngas generator 182.

A portion of the first hydrogen rich syngas stream 190a can be subjected to hydrogen separation unit 192 to generate a purified hydrogen by-product stream 164 and a second hydrogen rich syngas stream 190b. The second hydrogen rich syngas stream 190b has a hydrogen to carbon monoxide ratio greater than that of the hydrogen lean syngas stream 88 or 91 and less than that of the first hydrogen rich syngas stream 190a. In one embodiment the ratio of hydrogen to carbon monoxide in the second hydrogen rich syngas stream 190b can be in the range of 2:1 to 5:1.

Any portion of the hydrogen lean syngas stream 88 or 91, the first hydrogen rich syngas stream 190a and the second hydrogen rich syngas stream 190b, or any combination thereof, can be subjected to carbon dioxide removal unit 300 to generate purified hydrogen rich syngas stream 190c and a carbon dioxide byproduct stream 98a.

In one embodiment a combination of the hydrogen lean syngas stream 88 or 91, the first hydrogen rich syngas stream 190a and/or the second hydrogen rich syngas stream 190b is fed to the carbon dioxide removal unit 300.

In one embodiment, after removal of carbon dioxide, the first hydrogen rich syngas stream 190a and/or the second hydrogen rich syngas stream 190b can be combined with the hydrogen lean syngas stream 88 or 91 to obtain purified hydrogen rich syngas stream 190c and the carbon dioxide by-product stream 98a.

The first hydrogen rich syngas stream 190a and/or the second hydrogen rich syngas stream 190b is combined with the hydrogen lean syngas stream 88 or 91 before or after CO₂ removal to create an optimum Fischer-Tropsch syngas stream where the preferred ratio of the hydrogen to carbon monoxide is 2:1. The purified hydrogen rich stream 190c is then fed to the Fischer-Tropsch upgrader unit 128 to formulate synthesized hydrocarbons.

Any portion of the lean syngas stream 88 or 91, the first hydrogen rich syngas stream 190a, the second hydrogen rich syngas stream 190b, the purified hydrogen rich stream 190c, or any combination thereof, can be reacted with carbon dioxide by-product stream 98a, at least a portion of the purified hydrogen by-product stream 164 or a combination thereof to generate an optimum methanol feed stream to co-produce methanol 304 in methanol synthesis unit 302, in addition to the synthesized hydrocarbons as discussed above. The optimum feed stream for the methanol production involve the following reactions:

$$CO + 2H_2 = CH_3OH \text{ (primary reaction)}$$

$$CO_2 + 3H_2 = CH_3OH \text{ (secondary reaction)}$$

wherein the optimum stoichiometric ratio is defined as $(H_2-CO_2/CO+CO_2)=2.03$ In one embodiment, the acid gas 92 obtained after passing the sour hydrogen lean gas stream 88 through syngas treatment unit 90 can be further treated in sulfur plant 94 to generate elemental sulfur 96 and another carbon dioxide by-product stream 98b, which can be used in the production of methanol, alone or in combination with the carbon dioxide stream 98a as discussed above.

The purification of the first hydrogen rich stream 190a at hydrogen unit 192 can be achieved via pressure swing adsorption (PSA), membrane or liquid absorption technology, or by treating the first hydrogen rich syngas stream to a water gas shift (WGS) reaction prior to pressure swing adsorption (PSA), membrane or liquid absorption with optional removal of an additional CO₂ by-product stream 98c. The CO₂ by-product stream 98c can optionally be removed before as feed stream to PSA or after as tail gas from the PSA. The CO₂ by-product stream 98c is removed as a by-product of the membrane and liquid absorption steps. The CO₂ by-product stream 98c can be used in the production of methanol 304, alone or in combination with the carbon dioxide streams 98a and 98b as discussed above.

Figure 9:
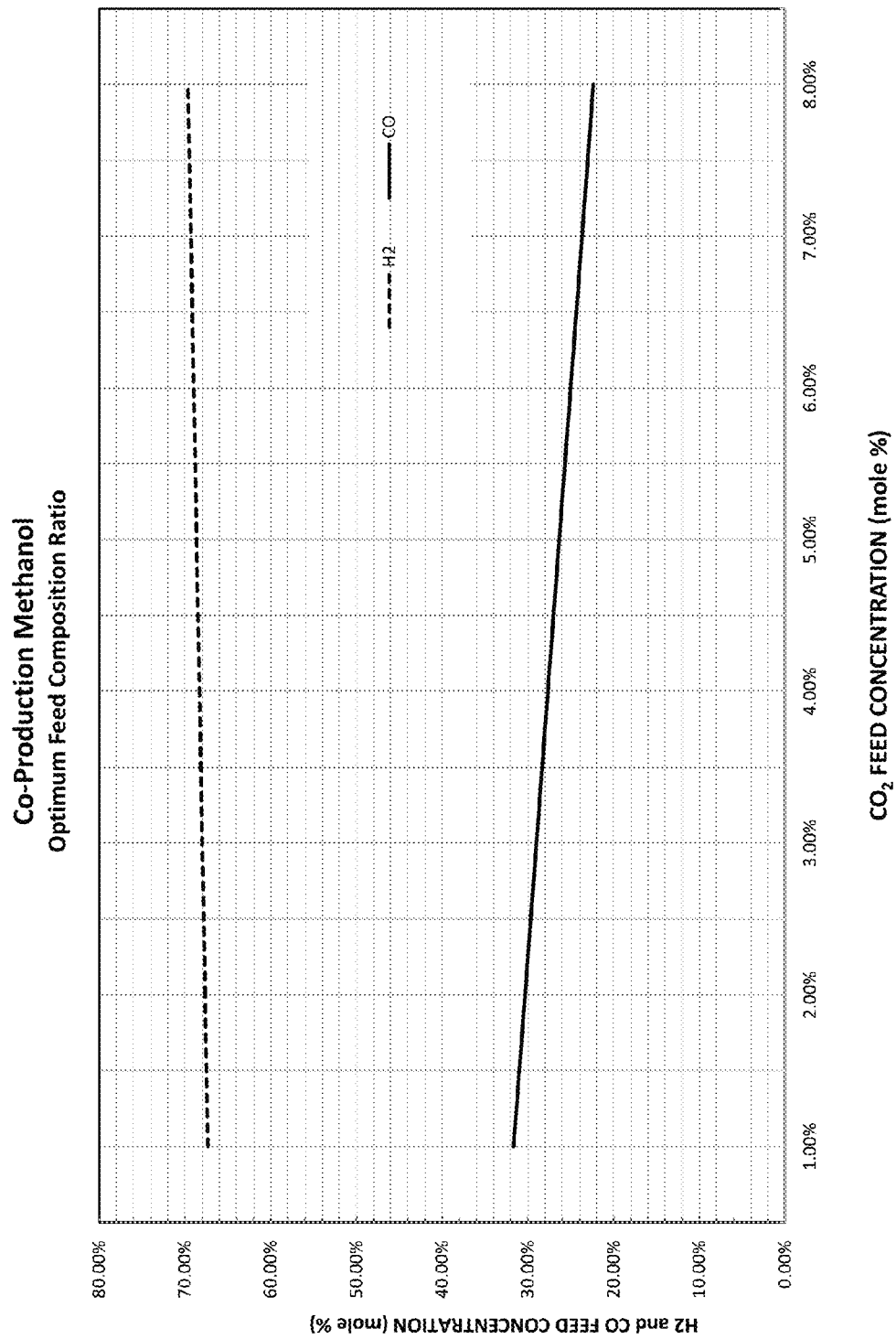
FIG. 9 is a chart illustrating the optimum feed composition for methanol production with the upgrading process in accordance with the present invention.

FIG. 9 describes the optimum composition for syngas feeding the methanol synthesis unit based on main active components CO, H₂ and CO₂, relative to the amount of CO₂ in the syngas.

Figure 10:
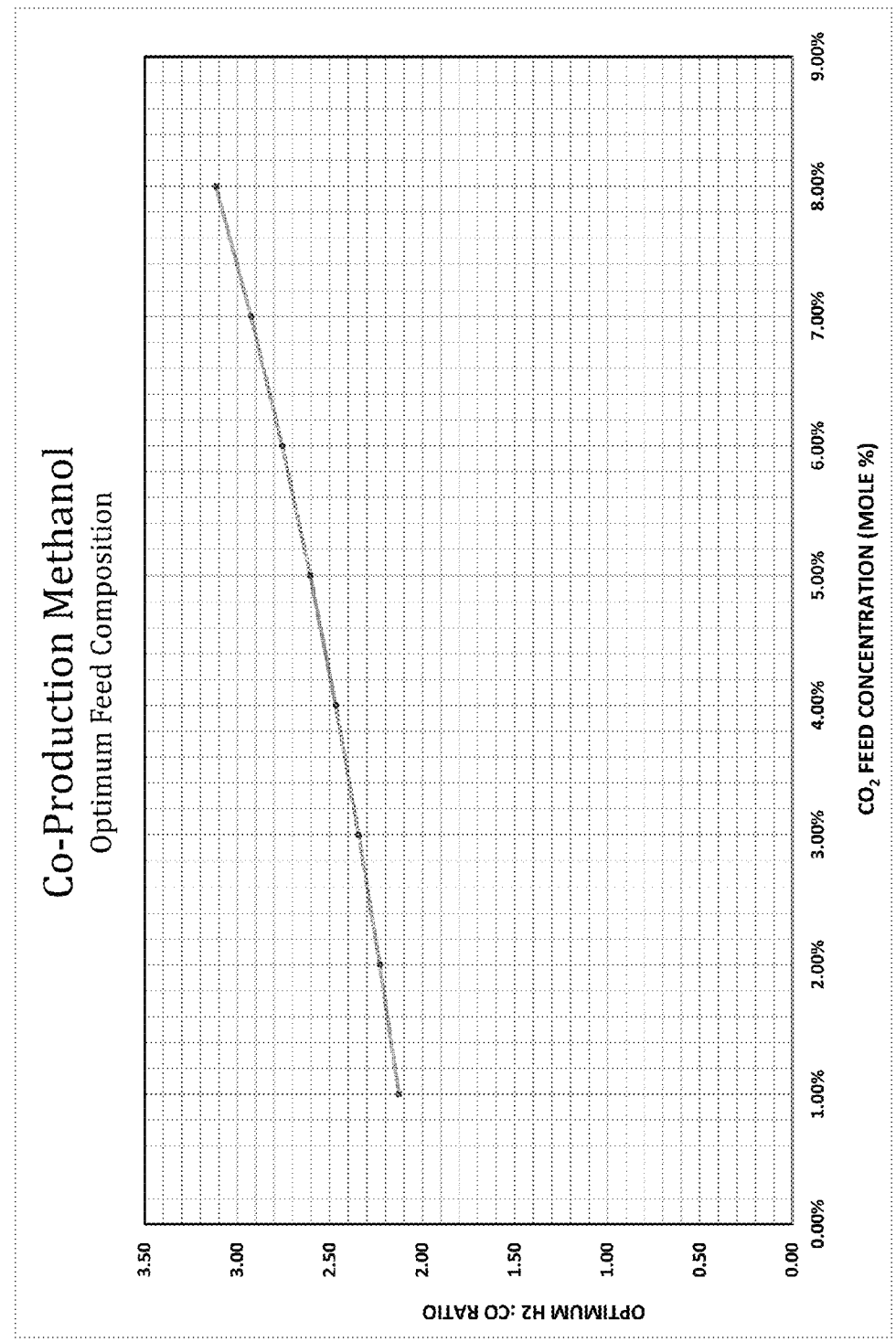
FIG. 10 is a chart illustrating the optimum stoichiometric $H_2$:CO feed ratio for methanol production with the upgrading process in accordance with the present invention.

FIG. 10 further describes the optimum syngas H₂:CO ratios relative to the amount of CO₂ in the syngas. It is noted that for all methanol syngas feed streams, where the CO₂ content is greater than zero (typical and preferred), the H₂:CO ratio is always greater than 2.0, which is the optimum for Fischer-Tropsch synthesis.

The high purity oxygen 124, typically greater than 95% purity, more preferred greater than 98% purity, for the partial oxidation reaction in the gasifier 86 and/or for use in the syngas generator 182, when the syngas generator comprises an ATR, and/or for use in sulfur recovery unit 94 to enrich the Claus process, can be generated by subjecting air to an air separation unit (ASU) 306, along with the generation of a nitrogen by-product stream 308.

Figure 11:
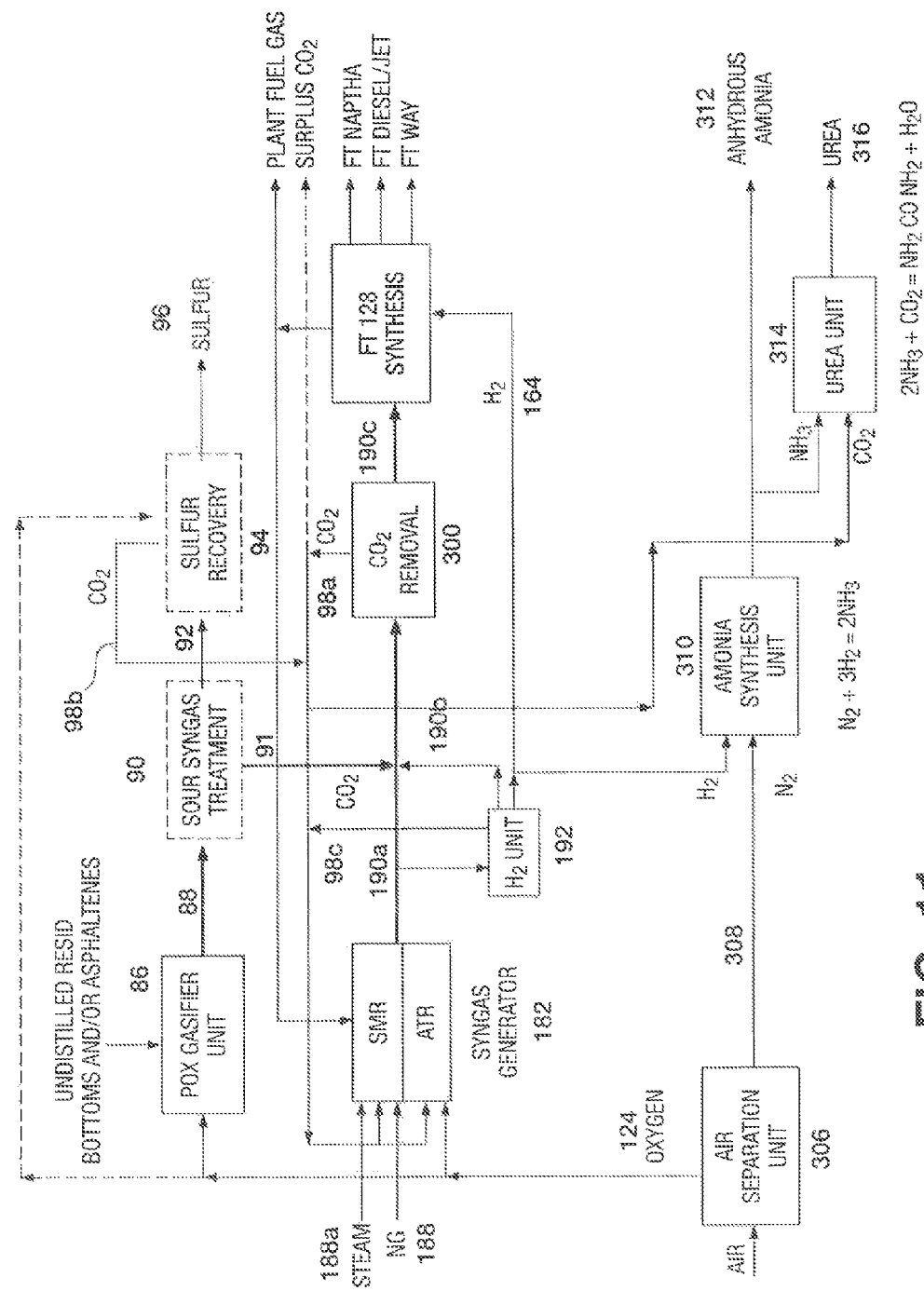
FIG. 11 is a process flow diagram illustrating integration of ammonia production with the upgrading process in accordance with the present invention.

FIG. 11 describes one configuration of the present invention whereby an Ammonia Synthesis Unit receives excess hydrogen feed 164 from the Hydrogen Separation Unit 192, and combined with the feed of nitrogen by-product N₂ 308, creates the optimum feed to produce anhydrous ammonia NH₃ co-product $$N_2 + 3H_2 = NH_3$$

With further processing and with the addition of by-product CO₂ from the upgrading/refinery process, urea can be co-produced as follows;

$$2NH_3 + CO_2 = NH_2CONH_2 + H_2O.$$

The process depicted in FIG. 11 is variation of the process flow diagram depicted in FIG. 8, wherein at least a portion of the purified hydrogen by-product stream 164 is reacted with the a portion of the nitrogen by-product stream 308 generated from the air separation unit 306, to produce ammonia 312 through an ammonia synthesis unit 310. The ammonia may then be optionally reacted with one or more of the carbon dioxide by-product streams 98a, 98b and 98c to produce urea 316 through a urea synthesis unit 314.

Figure 12:
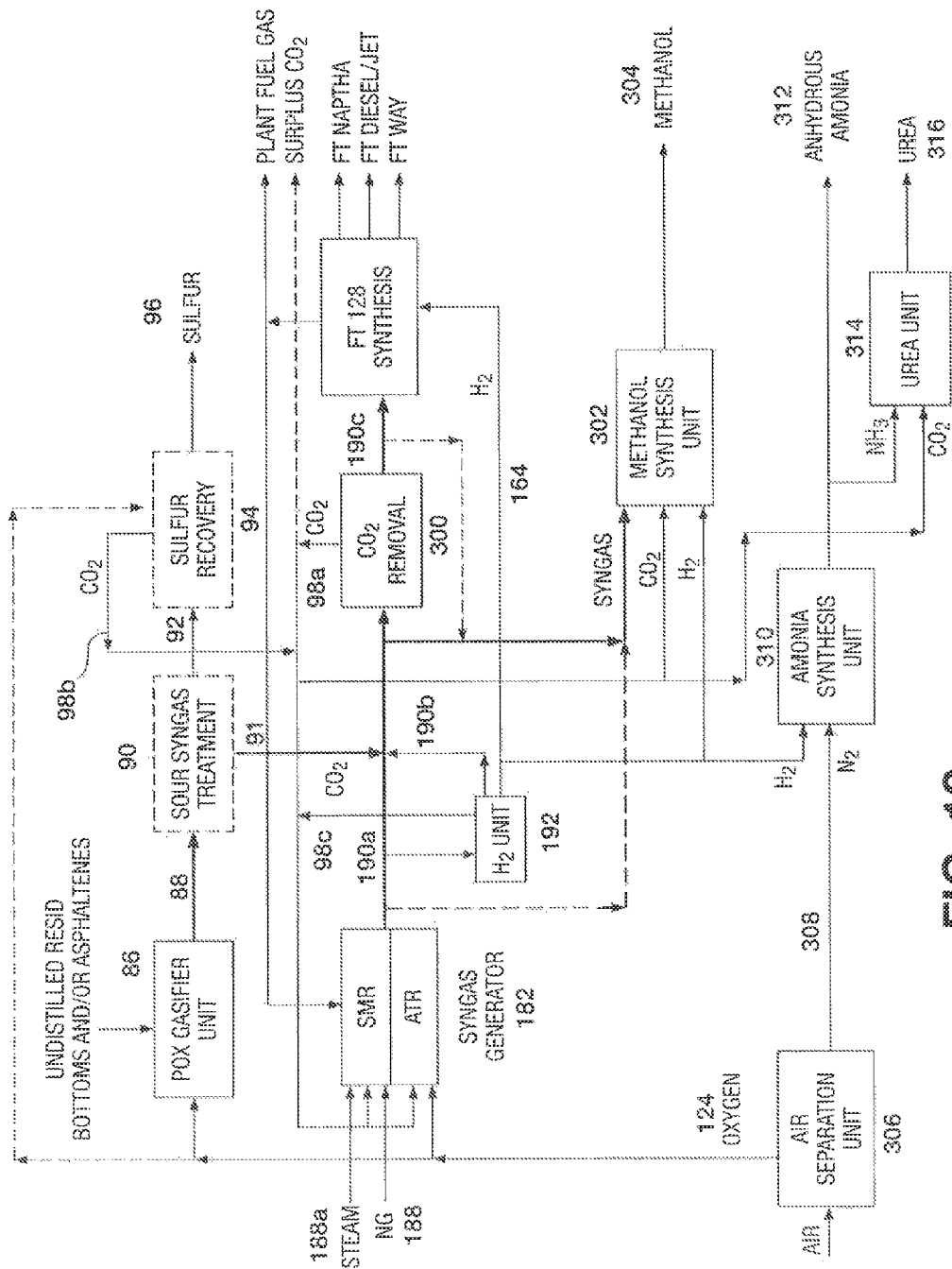
FIG. 12 is a process flow diagram illustrating integration of methanol and ammonia production with the upgrading process in accordance with the present invention.

FIG. 12 describes another configuration of the present invention whereby Ammonia and Methanol Synthesis Units 310 and 302 as described in FIGS. 11 and 8, respectively, are integrated with the heavy oil or bitumen upgrading plant as described in FIG. 6, and the combined processes produce synthetic diesel/jet, synthetic wax, ammonia and methanol, with optional further processing to obtain DME gasoline/diesel and urea fertilizer.

The following examples are based on a Alberta Athabasca Bitumen (API 8.5) deep conversion upgrader/refinery with 100,000 BPD feed capacity, configured generally as described in U.S. application Ser. No. 13/091,025, filed Apr. 20, 2011. This upgrader/refinery configuration is very efficient in retaining and converting carbon in bitumen and natural gas feed streams to refined products at an overall carbon conversion rate of about 90%. There is a by-product CO₂ stream 98a of about 1200 TPD available from the CO₂ Removal Unit 300 after the production of optimum rich hydrogen syngas stream 190c with H₂:CO ratio=2.0 for Fischer Tropsch synthesis (assuming minimal CO₂ in stream 190c). The following Examples describe how valuable commercial co-products are produced according to one embodiment of the present invention.

EXAMPLE 1

This example describes the design basis of a co-production Methanol Plant 302, whereby a portion of about 356 MMSCFD of stream 190c is removed from the Fischer-Tropsch synthesis feed and directed as the base feed to unit 302. It is further combined with about 656 TPD CO₂ from by-product stream 98a and about 40.6 MMSCFD H₂ from stream 164, the result would be the optimum feed for co-production of 5,000 TPD or 1,800,000 TPY of Methanol by-product. This is the current world scale commercial methanol plant.

a) Partial Stream 190c 356 MMSCFD or 39,035 moles/hr syngas with H₂:CO=2.0
b) Partial Stream 98a 656 TPD CO₂ or 1370 moles/hr CO₂
c) Partial Stream 164 40.6 MMSCFD H₂ or 4452 moles/hr H₂
d) The total syngas to Unit 302 44,856 moles/hr, or 67.94% H₂, 29.06% CO, 3.0% CO₂
e) Therefore, optimum syngas to Unit 302=(67.94−3.0)/29.06+3.0)=2.03
f) Total stream of 13,011 moles/hr CO+1,370 moles/hr CO₂+30,475 moles/hr H₂ results in 14,381 moles/hr CH₃OH or about 460,000 lb/hr=5,000 TPD or 1,800,000 TPY methanol

EXAMPLE 2

This example describes a design basis of a co-production Ammonia Plant 310, whereby the Air Separation Unit produces 2100 TPD of high purity oxygen 124 for the upgrader use. The subsequent by-product of nitrogen results in 8,300 TPD $N_2$ as stream 308. A portion of about 306 MMSCFD $H_2$ from stream 164 is combined with 4,194 TPD $N_2$, the result would be the optimum feed for the co-production of 5,000 TPD or 1,800,000 TPY of Ammonia by-product. This is the current world scale commercial ammonia plant.
   a) Partial Stream 308 consisting of 4,194 TPD $N_2$ or 11,333 moles/hr
   b) Partial Stream 164 consisting of 306 MMSCFD $H_2$ or 33,553 moles/hr $H_2$
   c) The total feed stream to Unit 310 of 44,886 moles/hr, or 25.2% $N_2$ and 74.8% $H_2$
   d) 11,333 moles/hr $N_2$+33,553 moles/hr $H_2$ results in 22,666 moles/hr $NH_3$ or about 453,320 lb/hr=5,000 TPD or 1,800,000 TPY ammonia

EXAMPLE 3

This example describes a design basis for a co-production Urea Plant 314, whereby a portion of the ammonia production 312 and additional by-product $CO_2$ from the upgrader/refinery (98a, b or c) is combined to produce urea fertilizer.
   a) Partial Stream 312 consisting of 4,202 TPD $NH_3$ or 19,048 moles/hr
   b) Remaining portion of Stream 98a consisting of 544 TPD $CO_2$ and Partial Stream 98c consisting of 4017 TPD $CO_2$ for total of 4,561 TPD $CO_2$ or 9,524 moles/hr $CO_2$
   c) The total feed stream to Unit 314 of 28,572 moles/hr, or 66.7% $NH_3$ and 33.3% $CO_2$
   d) 19,048 moles/hr $NH_3$+9,524 moles/hr $CO_2$ results in 9,524 moles/hr $NH_2CONH_2$ or about 628,584 lb/hr=6,800 TPD or 2,400,000 TPY urea The examples described above illustrate how the integration of the co-product units can recover a significant portion of the upgrader/refinery GHG $CO_2$ emissions and co-produce 5,000 TPD Methanol and 5,000 TPD Ammonia or 6,800 TPD of Urea, and result in a "Near Zero GHG Emissions World Class Upgrader/Refinery".

These embodiments of the present invention can be used with all existing and new grassroots upgraders and refineries of any scale which involve formulation of synthesized hydrocarbons as described in the processes disclosed herein to enhance performance and economics.

The net effect of the present invention is that the upgrading complex becomes:
   The lowest cost producer of upgraded/refined products and co-products such as ammonia and methanol.
   100% of all the carbon in feed streams and captured streams are converted to valuable commercial co-products.
   Upgrading Complex is "Near-Zero GHG Emission Green Upgrader/Refinery"-best in class.
   No production of wasteful byproducts such as petcoke, HSFO High Sulfur Fuel Oil and Resid, or asphalt/asphaltene.

While the preferred embodiments of the invention have been shown and described, modifications thereof can be made by one skilled in the art without departing from the spirit and teachings of the invention. Reactor design criteria, hydrocarbon processing equipment, and the like for any given implementation of the invention will be readily ascertainable to one of skill in the art based upon the disclosure herein. The embodiments described herein are exemplary only, and are not intended to be limiting. Many variations and modifications of the invention disclosed herein are possible and are within the scope of the invention. Use of the term "optionally" with respect to any element of a claim is intended to mean that the subject element is required, or alternatively, is not required. Both alternatives are intended to be within the scope of the claim.

Accordingly, the scope of protection is not limited by the description set out above, but is only limited by the claims which follow, that scope including all equivalents of the subject matter of the claims. Each and every claim is incorporated into the specification as an embodiment of the present invention. Thus the claims are a further description and are an addition to the preferred embodiments of the present invention. The discussion of a reference in the Background of the Invention is not an admission that it is prior art to the present invention, especially any reference that may have a publication date after the priority date of this application. The disclosures of all patents, patent applications and publications cited herein are hereby incorporated herein by reference, to the extent that they provide exemplary, procedural or other details supplementary to those set forth herein.

The invention claimed is:

1. A process for co-producing commercially valuable products from by-products of a process for upgrading or refining heavy oil or bitumen to formulate synthesized hydrocarbons, comprising:
   (a) forming a non-distilled bottom fraction from a source of heavy oil or bitumen feedstock;
   (b) feeding said bottom fraction to a syngas generating circuit for formulating a hydrogen lean syngas stream via a non-catalytic partial oxidation reaction;
   (c) providing a first hydrogen rich syngas stream from a syngas generator;
   (d) subjecting a portion of said first hydrogen rich syngas stream to a hydrogen separator unit to provide a purified hydrogen by-product stream and a second hydrogen rich syngas stream;
   (e) subjecting at least a portion of said hydrogen lean syngas stream, said first hydrogen rich syngas stream, said second hydrogen rich syngas stream or a combination thereof, to a carbon dioxide removal operation to obtain a purified hydrogen rich syngas stream an a carbon dioxide by-product stream;
   (f) reacting said purified hydrogen rich syngas stream in a Fischer-Tropsch reactor to formulate synthesized hydrocarbons; and
   (g) converting said purified hydrogen by-product stream and/or said carbon dioxide by-product stream into said commercially valuable co-products.

2. The process according to claim 1, wherein said valuable co-products are selected from the group consisting of methanol, ammonia, urea or any combination thereof.

3. The process as set forth in claim 1, wherein said hydrogen rich syngas generator is selected from the group consisting of a steam methane reformer (SMR), autothermal reformer (ATR), any series or parallel combination thereof and a hybrid combination thereof (XTR).

4. The process according to claim 1, comprising subjecting air to an air separation unit to generate a nitrogen stream and an oxygen stream, wherein said oxygen stream is for the non-catalytic partial oxidation reaction and optionally for the syngas generator when said generator comprises an ATR and/or optionally for enriching a sour syngas treatment operation.

5. The process according to claim 1, wherein said commercially valuable co-product is methanol, which is obtained by reacting a portion of said first hydrogen rich syngas stream, said second hydrogen rich syngas stream, said hydrogen lean syngas stream, said purified hydrogen rich syngas stream, or a combination thereof, with said $CO_2$ by-product stream, at least a portion of said purified hydrogen by-product stream or a combination thereof.

6. The process according to claim 4, wherein said commercially valuable co-product is ammonia, which is obtained by reacting said nitrogen stream with at least a portion of said purified hydrogen by-product stream.

7. The process according to claim 6, wherein said ammonia is reacted with said $CO_2$ by-product stream to form urea.

8. The process according to claim 1, wherein said purified hydrogen rich syngas stream is obtained by purification of at least a portion of said first hydrogen rich syngas stream via pressure swing adsorption, membrane or liquid absorption, or by treating at least a portion of said first hydrogen rich syngas stream to a water gas shift (WGS) reaction prior to pressure swing adsorption, membrane or liquid absorption with optional removal of an additional $CO_2$ by-product stream from the said second hydrogen rich syngas stream.

9. The process according to claim 8, wherein the additional $CO_2$ by-product stream is used for conversion into said commercially valuable co-products.

10. The process according to claim 1, wherein said bottom fraction is converted to a sour hydrogen lean syngas stream.

11. The process according to claim 10, further including the step of treating said sour hydrogen lean syngas stream to the said sour syngas treatment operation to form a sweet hydrogen lean syngas stream and an additional $CO_2$ by-product stream for conversion into said commercially valuable co-products.

12. The process according to claim 1, wherein said synthesized hydrocarbons include at least one of Fischer-Tropsch vapours, paraffinic naphtha, light Fischer-Tropsch liquid, heavy Fischer-Tropsch liquid, or Fischer-Tropsch wax.

13. The process according to claim 12, wherein said Fischer-Tropsch vapours are further treated to a $CO_2$ removal operation to form an additional $CO_2$ by-product stream for conversion into said commercially valuable co-products.

14. The process according to claim 12, further including the step of processing said synthesized hydrocarbons in a hydroprocessing unit.

15. The process according to claim 14, wherein said hydroprocessing unit includes at least one operation selected from the group consisting of hydrocracking, thermocracking, hydrotreating, isomerization, fractionation and combinations thereof.

16. The process according to claim 1, wherein $CO_2$ is further captured in a $CO_2$ removal operation from flue gas streams resulting from furnaces, boilers, power generation and any other combustion units used in the upgrader to form an additional $CO_2$ by-product stream for conversion into said commercially valuable co-products.

17. The process according to claim 1, wherein $CO_2$ is further provided from any other external source other than the upgrader to form an additional $CO_2$ by-product stream for conversion into said commercially valuable co-products.

18. The process according to claim 1, wherein the bitumen and heavy oil upgrader is capable of near zero green house gas $CO_2$ emissions.

19. The process according to claim 1, wherein said bitumen is an in situ source.

20. The process according to claim 1, wherein said bitumen is a mineable source.

* * * * *